(12) United States Patent
Bonda et al.

(10) Patent No.: US 8,070,989 B2
(45) Date of Patent: *Dec. 6, 2011

(54) PHOTOSTABILIZATION OF RETINOIDS WITH ALKOXYCRYLENE COMPOUNDS

(75) Inventors: Craig A. Bonda, Winfield, IL (US); Anna Pavlovic, Elmwood Park, IL (US); Jean Zhang, Hickory Hills, IL (US)

(73) Assignee: Hallstar Innovations Corp., Chicago, IL (US)

( * ) Notice: Subject to any disclaimer, the term of this patent is extended or adjusted under 35 U.S.C. 154(b) by 67 days.

This patent is subject to a terminal disclaimer.

(21) Appl. No.: 12/533,598

(22) Filed: Jul. 31, 2009

(65) Prior Publication Data

US 2009/0324570 A1    Dec. 31, 2009

Related U.S. Application Data

(63) Continuation-in-part of application No. 12/022,758, filed on Jan. 30, 2008, now Pat. No. 7,588,702, which is a continuation-in-part of application No. 11/891,281, filed on Aug. 9, 2007, now Pat. No. 7,597,825.

(51) Int. Cl.
| | |
|---|---|
| F21V 9/04 | (2006.01) |
| F21V 9/06 | (2006.01) |
| G02B 5/22 | (2006.01) |
| G02B 5/26 | (2006.01) |
| A61K 38/43 | (2006.01) |
| A61K 8/00 | (2006.01) |
| A61K 8/18 | (2006.01) |
| A61Q 17/04 | (2006.01) |

(52) U.S. Cl. ............ 252/589; 424/59; 424/60; 424/401; 424/94.1; 514/337; 514/532; 514/557; 514/569; 514/703; 524/90; 558/410; 546/280.1; 560/61; 562/471; 562/490; 562/510; 568/446; 568/823

(58) Field of Classification Search .................... 424/59, 424/60, 94.1; 558/410; 560/81, 61; 568/446, 568/823; 562/510, 471, 490; 546/280.1; 514/569, 337, 532, 557, 703, 729
See application file for complete search history.

(56) References Cited

U.S. PATENT DOCUMENTS

| | | |
|---|---|---|
| 2,623,060 A | 12/1952 | Cragoe |
| 3,215,724 A | 11/1965 | Strobel et at. |
| 3,337,357 A | 8/1967 | Strobel et al. |
| 4,284,621 A | 8/1981 | Preuss et al. |
| 4,293,542 A | 10/1981 | Lang et al. |
| 4,307,240 A | 12/1981 | Ching |
| 4,396,240 A | 8/1983 | Henson |
| 4,562,278 A | 12/1985 | Hill |
| 4,617,374 A | 10/1986 | Pruett et al. |
| 4,707,537 A | 11/1987 | Pruett et al. |
| 5,576,354 A | 11/1996 | Deflandre et al. |
| 5,663,213 A | 9/1997 | Jones et al. |
| 5,738,842 A | 4/1998 | Raspanti et al. |
| 5,783,307 A | 7/1998 | Fagerburg et al. |
| 5,989,528 A | 11/1999 | Tanner et al. |
| 5,993,789 A | 11/1999 | Bonda et al. |
| 6,113,931 A | 9/2000 | Bonda et al. |
| 6,225,052 B1 | 5/2001 | Batz et al. |
| 6,284,916 B1 | 9/2001 | Bonda et al. |
| 6,485,713 B1 | 11/2002 | Bonda et al. |
| 6,518,451 B2 | 2/2003 | Bonda et al. |
| 6,537,529 B1 | 3/2003 | Bonda |
| 6,551,605 B2 | 4/2003 | Bonda |
| 6,800,274 B2 | 10/2004 | Bonda et al. |
| 6,890,521 B2 | 5/2005 | Bonda |

(Continued)

FOREIGN PATENT DOCUMENTS

DE      1222926      8/1966

(Continued)

OTHER PUBLICATIONS

*Amoco® NDC for Coatings, Inks and Adhesives*, Amoco Chemicals, Bulletin FA-21b, dated N-9, Jun. 2001.
*Light Absorbing Properties of Naphthalate Containing Polyesters*, BP p.l.c. Technical Bulletin N-10 (2001).
Baussard, "Chap. II: Donor-Acceptor pairs for Forster Resonance Energy Transfer (FRET)" in *Synthesis of New Ionic Functional Polymers by Free Radical Polymerization via the RAFT Process*, Dissertation, Catholic University of Louvain, (Jan. 26, 2004).

(Continued)

*Primary Examiner* — Ling Choi
*Assistant Examiner* — Bijan Ahvazi
(74) *Attorney, Agent, or Firm* — Marshall, Gerstein & Borun LLP

(57) ABSTRACT

The photostabilizing electronic excited state energy—particularly singlet state energy from retinoid compounds—has been found to be readily transferred to (accepted by) α-cyanodiphenylacrylate compounds having an alkoxy radical in the four (para) position (hereinafter "alkoxycrylenes") on one of the phenyl rings having the formula (I):

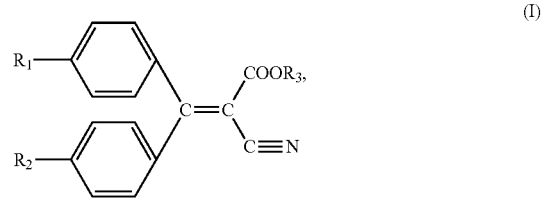

(I)

wherein one of $R_1$ and $R_2$ is a straight or branched chain $C_1$-$C_{30}$ alkoxy radical, preferably $C_1$-$C_8$, more preferably methoxy, and the non-alkoxy radical $R_1$ or $R_2$ is hydrogen; and $R_3$ is a straight or branched chain $C_1$-$C_{30}$ alkyl radical, preferably $C_2$-$C_{20}$. The alkoxycrylene compounds of formula (I) significantly increase the photostability of retinoid compounds in a composition by at least 3-fold and as much as 10-fold or greater. The ability of the alkoxycrylene compounds to stabilize the retinoid compound is concentration dependent, with the amount of retinoid photostabilization increasing with the concentration of the alkoxycrylene compound.

31 Claims, 1 Drawing Sheet

U.S. PATENT DOCUMENTS

| | | | |
|---|---|---|---|
| 6,905,525 B2 | 6/2005 | Wood et al. | |
| 6,919,473 B2 | 7/2005 | Bonda et al. | |
| 6,962,692 B2 | 11/2005 | Bonda et al. | |
| 7,064,114 B2 | 6/2006 | Yiv et al. | |
| 7,201,893 B2 | 4/2007 | Wendel et al. | |
| 7,235,587 B2 | 6/2007 | Bonda et al. | |
| 7,292,156 B2 | 11/2007 | Smith et al. | |
| 7,449,698 B2 | 11/2008 | Nguyen et al. | |
| 7,534,420 B2 | 5/2009 | Bonda et al. | |
| 7,588,702 B2 * | 9/2009 | Bonda et al. | 252/589 |
| 7,597,825 B2 * | 10/2009 | Bonda et al. | 252/589 |
| 2002/0127192 A1 | 9/2002 | Murphy et al. | |
| 2003/0176542 A1 * | 9/2003 | Abe et al. | 524/91 |
| 2004/0047817 A1 | 3/2004 | Bonda | |
| 2004/0057914 A1 * | 3/2004 | Bonda et al. | 424/59 |
| 2004/0170579 A1 | 9/2004 | Mobius | |
| 2006/0062746 A1 * | 3/2006 | Brillouet et al. | 424/59 |
| 2006/0228311 A1 | 10/2006 | Bonda et al. | |
| 2008/0286217 A1 | 11/2008 | Chaudhuri et al. | |
| 2009/0057627 A1 * | 3/2009 | Bonda et al. | 252/601 |

FOREIGN PATENT DOCUMENTS

| | | |
|---|---|---|
| EP | 0570838 | 11/1993 |
| EP | 0761201 | 3/1997 |
| EP | 1323743 | 7/2003 |
| JP | 08225672 | 9/1996 |
| JP | 2005139263 | 6/2005 |
| SU | 1273360 | 11/1986 |
| WO | WO-00/27337 | 5/2000 |
| WO | WO-02/42368 | 5/2002 |
| WO | WO-2007/128840 | 11/2007 |

OTHER PUBLICATIONS

Bonda, "Research pathways to photostable sunscreens," *Cosmetics & Toiletries Magazine*, 123:1, 49-60 (Feb. 5, 2008).

Chatelain et al., "Photostabilization of butyl methoxydibenzoylmethane (Avobenzone) and ethylhexyl methoxycinnamate by bis-ethylhexyloxyphenol methoxyphenyl triazine (Tinosorb S), a new UV broadband filter", *Photochemistry and Photobiology*, 74(3):401-6 (2003).

Cheung, "Photophysical processes in dimethyl 2,6-naphthalenedicarboxylate and poly(ethylene 2,6-naphthalenedicarboxylate)" *J. Polymer Sci.: Polymer Let. Ed.*, 17:227-32 (1979).

European Search Report for EP 08103204.7, dated Jul. 25, 2008.

European Search Report for EP 08 10 205, dated Jul. 14, 2008.

Horiba Jobin Yvon Ltd., *A Guide to Fluorescence Quantum Yields*, www.jyhoriba.co.uk., dated Dec. 16, 2006.

International Search Report and Written Opinion or PCT/US/2008/058454, dated Sep. 23, 2008.

International Search Report and Written Opinion or PCT/US2008/058456, dated Jun. 27, 2008.

Karitzky et al., "Synthesis of 3,3-diarylpyrrolidines from diaryl ketones", *ARKIVOC*, (Gainesville, FL, United States), 5:9-18 (2003) URL: http://arkatusa.org/zark/journal/2003/Bernath/GB-594J/594J.pdf.

Min et al., "Spectroscopic studies on the interaction of cinnamic acid and its hydroxyl derivatives with human serum albumin", *J. Mol. Structure*, 692:71-80 (2004).

Palm et al., "Update on photoprotection" *Dermatologic Therapy*, 20:360-76 (2007).

Senchenya et al., "Silicon-containing esters of α-cyanoacrylic acid: synthesis and properties", *Russian Chem. Bul.*, 42:909-11 (1993).

Somsen et. al., "Planar chromatography coupled with spectroscopic techniques", *J. Chromatography A*, 703:613-65 (1995).

Turro et al., *Modern Molecular Photochemistry*, Chapter 9, University Science Books (1991).

* cited by examiner

PHOTOSTABILIZATION OF RETINOIDS WITH ALKOXYCRYLENE COMPOUNDS

CROSS-REFERENCE TO RELATED APPLICATIONS

This application is a continuation-in-part of U.S. Pat. application Ser. No. 12/022,758 filed on Jan. 30, 2008 now U.S. Pat. No. 7,588,702, which is a continuation-in-part of U.S. patent application Ser. No. 11/891,281 filed on Aug. 9, 2007 now U.S. Pat. No. 7,597,825, the disclosures of which are incorporated by reference in their entirety into the present application.

FIELD OF THE INVENTION

The present invention is directed to compositions and methods to increase the photostability of retinoid compounds. More particularly, the invention relates to the photostabilization of isotretinoin and retinol with alkoxycrylene compounds.

BACKGROUND

The retinoids are a class of chemical compounds that are structurally related to vitamin A. Retinoid compounds have many important and diverse functions throughout the body including roles in vision, regulation of cell proliferation and differentiation, growth of bone tissue, immune function, and activation of tumor suppressor genes. Retinoid compounds are also being researched as treatments for skin cancer. For example, 9-cis-retinoic acid is used topically to help treat skin lesions from Kaposi's sarcoma.

Retinoid compounds consist of four isoprenoid units joined in a head-to-tail manner. The basic structure of a retinoid compound includes a cyclic end group, a polyene side chain and a polar end group. The conjugation (i.e. alternating single and double bonds) of the polyene side chain is responsible for the color of retinoid compounds (typically yellow, orange, or red) and their ability to act as chromophores. Variations in the side chain and polar end group of these compounds lead to different classes of retinoid compounds.

Retinoid compounds are classified into three generations. First and second generation retinoid compounds are capable of binding to several retinoid receptors due to the flexibility imparted by their polyene side chain. Third generation retinoid compounds are less flexible than the first and second generation retinoid compounds and interact with fewer retinoid receptors. Examples of retinoid compounds are shown in Table 1.

TABLE 1

Examples of Retinoid Compounds

| | | |
|---|---|---|
| First Generation | Retinol | (structure) |
| | Retinal | (structure) |
| | All-trans-Retinoic Acid (Tretinoin, Retin-A) | (structure) |
| | 13-cis-Retinoic Acid (Isotretinoin) | (structure) |
| | 9-cis-Retinoic Acid (Alitretinoin) | (structure) |

TABLE 1-continued

Examples of Retinoid Compounds

Second Generation  Etretinate

Acitretin

Third Generation  Bexarotene

Tazarotene

Adapalene

Isotretinoin (13-cis-retinoic acid) is a retinoid compound with anti-inflammatory and anti-tumor action. This action is mediated through the beta and alpha retinoic acid receptors (RAR-β, RAR-α). Isotretinoin attenuates iNOS expression and activity in cytokine-stimulated murine mesangial cells. It induces mitochondrial membrane permeability transition, observed as swelling and as a decrease in membrane potential, and stimulates the release of cytochrome c implicating mechanisms through the apoptosis pathway. These activities are reversed by EGTA and cyclosporine A. Isotretinoin also increases MMP-1 protein expression partially via increased transcription. Isotretinoin is used in oral and topical anti-acne medications and in topical medications that are used to treat sun-damaged skin.

Retinol is an endogenous retinoid compound that helps in vision, bone growth, reproduction, growth of epithelium cells, and fighting infections. Once retinol has been taken up by a cell, it can be oxidized to retinal, which is further oxidized to retinoic acid. Retinoic acid acts as a ligand for both the RAR and the retinoid X receptor (RXR). Retinol appears to function in maintaining normal skin health and is often used in high price consumer products for treating aged and wrinkled skin.

Tretinoin has been shown to both treat acne and reverse some of the changes in the skin due to photo-aging, i.e. sun damage. If used long term, tretinoin may reduce some fine wrinkles, freckles, comedones (whiteheads and blackheads), and solar keratoses (dry scaly sun-spots). With prolonged use, tretinoin protects the skin against harmful UVB and UVA rays (Bhawan et al., 1996).

When using topical retinoid compounds, patients should be advised to incorporate preventative, healthy practices with respect to exposure to the sun. Damaging rays from the sun can penetrate the clouds and even glass. Therefore, people working by a window or riding in a vehicle also risk exposure to damaging rays. Sunscreens are considered the gold standard for protecting the skin from the harmful effects of UV light (Leyden, 2003), and a broad spectrum (UVB/UVA) sunscreen with key ingredients such as Avobenzone provides the most protection. Sunscreen should be applied daily, even on cloudy days and during the winter months. Patients should protect exposed areas of the skin with an appropriate sunscreen 30 minutes prior to exposure, followed by a second application to ensure adequate coverage. Often, once-a-day sunscreen application is not enough and sunscreen should be reapplied throughout the day. When exposed to the elements, sunscreen application is recommended to be applied every 2 hours and more often if sweating or swimming. When feasible, peak hours of the sun should be avoided (10 am to 4 pm), and patients should seek shade when they can. A sun-protection lip balm is also beneficial. If prolonged sun exposure is expected, such as during a vacation, the use of the topical retinoid compound should be discontinued one week before the exposure and resumed upon return.

One major drawback to the clinical use of retinoid compounds, especially topically as anti-acne, anti-aging, and wrinkle-reducing applications described herein, is the high reactivity of the conjugated polyene tail towards light. The absorption of ultraviolet light by a chromophore-containing organic molecule causes the excitation of an electron in the chromophore moiety from an initially occupied, low energy orbital to a higher energy, previously unoccupied orbital. The energy of the absorbed photon is used to energize an electron and cause it to "jump" to a higher energy orbital, see Turro, Modern Molecular Photochemistry, 1991. Two excited electronic states derive from the electronic orbital configuration produced by UV light absorption. In one state, the electron spins are paired (antiparallel) and in the other state the electron spins are unpaired (parallel). The state with paired spins has no resultant spin magnetic moment, but the state with unpaired spins possesses a net spin magnetic moment. A state with paired spins remains a single state in the presence of a magnetic field, and is termed a singlet state. A state with unpaired spins interacts with a magnetic field and splits into three quantized states, and is termed a triplet state.

In the electronically excited state, the chromophore-containing organic molecule is prone to degrade via a number of known pathways and, therefore, can absorb little or no additional UV light. To photostabilize an electronically excited chromophore-containing organic molecule in order to provide sufficient UV protection, it must be returned to the ground state before it undergoes a photochemical reaction destructive to its UV absorbing capability. There are known photostabilizing sunscreen additives, such as octocrylene, methylbenzilydene camphor, and the esters or polyesters of naphthalene dicarboxylic acid of this assignee's U.S. Pat. Nos. 6,113,931; 6,284,916; 6,518,451; and 6,551,605, all hereby incorporated by reference, that are capable of quenching excited triplet state energy. As shown in this assignee's pending application Ser. Nos. 11/891,281 and 12/022,758 filed on Aug. 9, 2007 and Jan. 30, 2008, respectively, the disclosure of which are hereby incorporated by reference, it has also been found that alkoxycrylenes, particularly methoxycrylenes, return chromophore-containing organic molecules, particularly butyl methoxydibenzoylmethane (Avobenzone), octyl methoxycinnamate (Octinoxate), and octyl salicylate (Octisalate), from both an electronically excited singlet state and excited triplet state back to their ground state, thereby photostabilizing the UV-absorbing organic molecules.

When retinoid compounds are exposed to light, they also undergo photodegradation via a number of pathways, including undesirable isomerization reactions, photoaddition/substitution reactions, and cycloadditions, all of which destroy the integrity of the retinoid and its ability to function as intended. For example, isotretinoin normally absorbs ultraviolet radiation strongly ($\epsilon$=44,000) with a peak at 366 nm (FIG. 1). After isotretinoin is exposed to 5 MED (105 mJ/cm$^2$) of UV radiation, which is equal to about one hour's worth of exposure to sunlight, the amount of isotretinoin decreases significantly (FIG. 2).

This photoinstability of retinoid compounds is highly problematic when developing and using topical retinoid compounds and retinoid compound-containing compositions for clinical purposes. To reduce the amount of photodegradation that occurs in topical retinoid compound-containing products, manufacture of the retinoid product must occur in the dark or under special lighting conditions, and the packaging of the retinoid product must be light fast. Even if retinoid compound-containing products are manufactured in the dark and stored in a light fast package, they quickly degrade upon application to the skin, rendering the retinoid product ineffective.

SUMMARY

The photostabilizing electronic excited state energy—particularly singlet state energy from a UV-absorbing molecule—has been found to be readily transferred to (accepted by) α-cyanodiphenylacrylate compounds having an alkoxy radical in the four (para) position (hereinafter "alkoxycrylenes") on one of the phenyl rings having the formula (I):

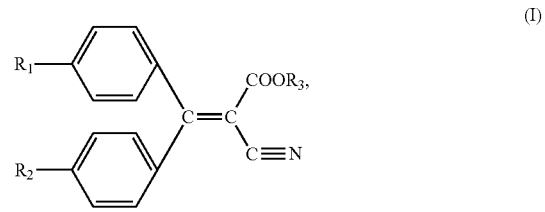

wherein one of $R_1$ and $R_2$ is a straight or branched chain $C_1$-$C_{30}$ alkoxy radical, preferably $C_1$-$C_8$, more preferably methoxy, and the non-alkoxy radical $R_1$ or $R_2$ is hydrogen; and $R_3$ is a straight or branched chain $C_1$-$C_{30}$ alkyl radical, preferably $C_2$-$C_{20}$.

It has surprisingly been found that the alkoxycrylene compounds of formula (I), described herein, significantly increase the photostability of retinoid compounds in a composition by at least 3-fold and as much as 10-fold or greater. The ability of the alkoxycrylene compounds to stabilize the retinoid compound is concentration dependent, with the amount of retinoid photostabilization increasing with the concentration of the alkoxycrylene compound.

DETAILED DESCRIPTION OF THE PREFERRED EMBODIMENTS

Figure 1:
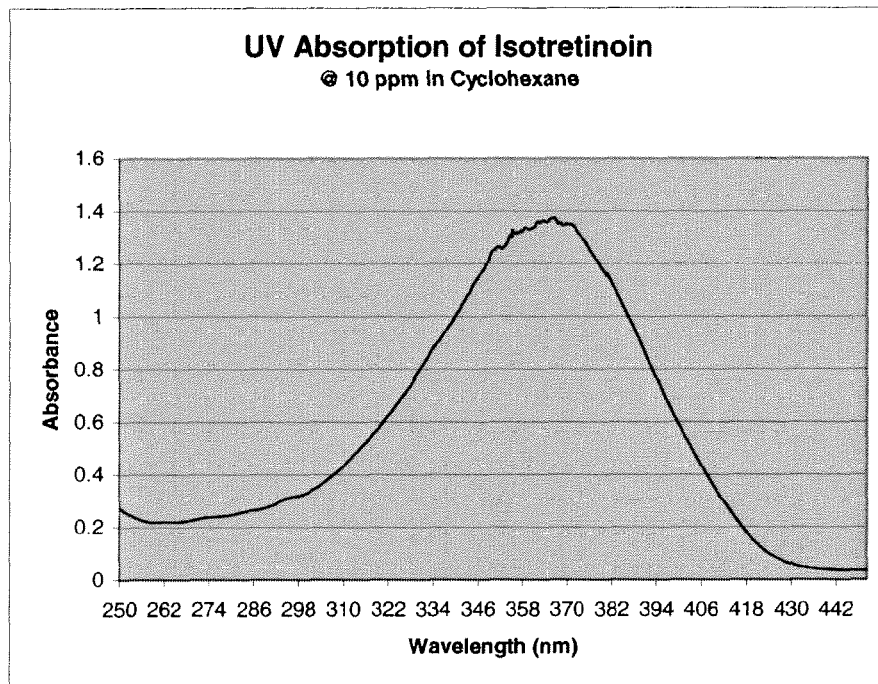
FIGS. 1 and 2 are graphs showing the UV absorbance of a composition containing 0.05% isotretinoin (10 ppm) in cyclohexane before (FIG. 1) and after (FIG. 2) exposure to 5 MED (105 mJ/cm$^2$) of UV radiation (290 to 400 nm).
Figure 2:
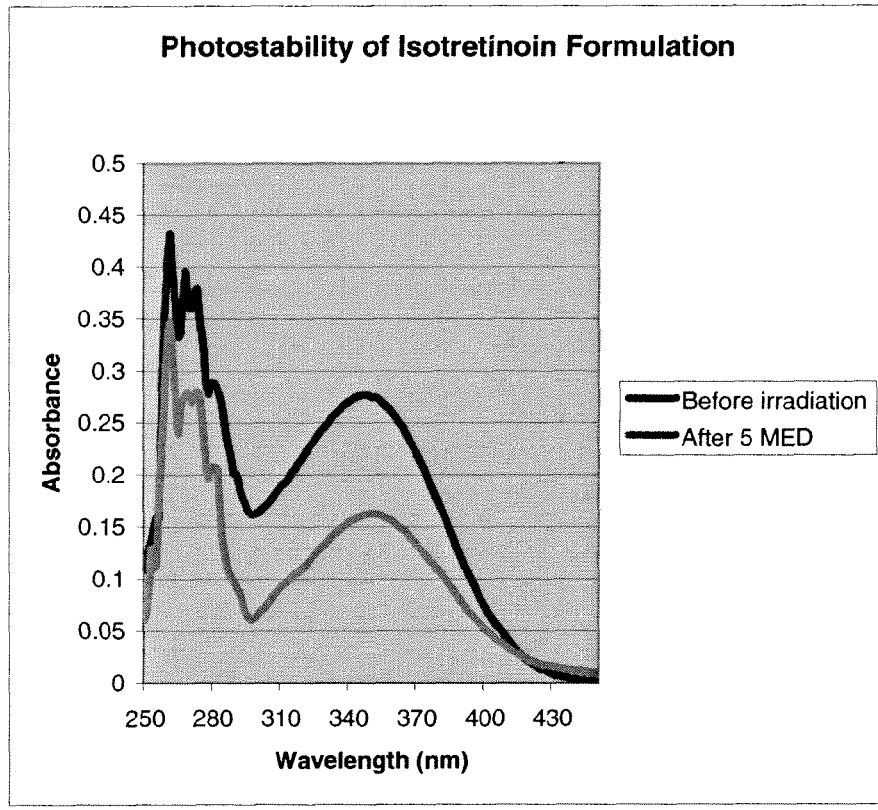

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The term "alkoxy" herein refers to a radical extending from the para position of one or both of the phenyl rings having the formula O—R, wherein R is an alkyl radical, straight chain or branched having 1 to 30 carbon atoms, preferably wherein R=$C_1$ to $C_8$, more preferably $C_2$-$C_{20}$, and most preferably —O—$CH_3$ (methoxy). The oxygen atom of the alkoxy radical is covalently bonded to the para carbon atom of one or both of the phenyl rings, preferably only one of the phenyls, preferably having the formula (II) or (III):

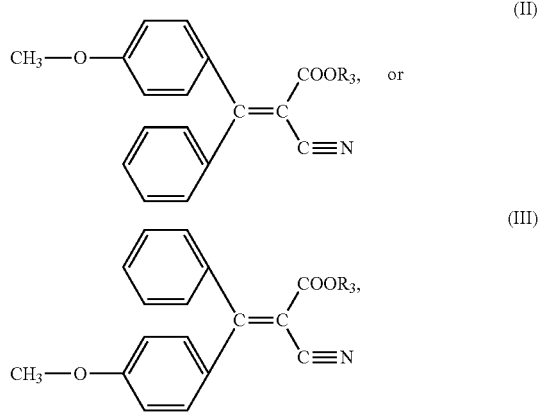

wherein $R_3$ is a straight or branched chain $C_1$-$C_{30}$ alkyl radical, preferably $C_2$-$C_{20}$.

The term "crylene" as used herein refers to a chromophoric moiety that includes an α-cyano-β,β-diphenyl propanoic acid ester.

The term "cyano" as used herein refers to a —C≡N group, also designated "—CN."

The term "minimal erythemal dose" (MED) is the minimum amount of UVB that produces redness 24 hours after exposure (1 MED=21 mJ/$cm^2$). A MED of 5 is approximately equivalent to about 1 hour in the sun.

The abbreviations used herein are defined in Table 2.

TABLE 2

| Abbreviation | Name |
| --- | --- |
| | Abbreviations |
| BHT | Butylhydroxytoluene |
| BOMeOC | Butyloctyl methoxycrylene |
| EDTA | Ethylenediaminetetraacetic acid |
| EGTA | Ethylene glycol tetraacetic acid |
| EHMC | Ethylhexyl methoxycrylene |
| HPLC | High-performance liquid chromatography |
| IsoRA | Isotretinoin (13-cis-retinoic acid) |
| MED | Minimal erythemal dose |
| O/W | Oil-in-water emulsion |
| PEG | Polyethylene glycol |
| PTFE | Polytetrafluoroethylene |

TABLE 2-continued

| Abbreviation | Name |
| --- | --- |
| | Abbreviations |
| Q.S. | Quantum sufficiat (as much as suffices) |
| UV | Ultraviolet |
| UVR | Ultraviolet radiation |

Compositions that contain one or more retinoid compounds, for treating skin, for example as anti-acne or wrinkle reduction treatment, advantageously also generally include UV-A and UV-B photoactive compounds in a dermatologically acceptable carrier, optionally including additives, such as emollients, stabilizers, emulsifiers, and combinations thereof. These additives can be used in preparing a UV filter composition, containing one or more retinoid compounds in an emulsion (oil-in-water or water-in-oil) from a composition that includes one or more photoactive compounds and a solvent or a solvent combination that includes one or more organic solvents and water. When made, preferably the emulsion is an oil-in-water (O/W) emulsion, wherein the oil phase is primarily formed from a mixture of the UV filter compound(s) and one or more organic solvents.

The retinoid compound-containing composition advantageously includes one or more photoactive compounds, in addition to the retinoid compound(s), wherein the photoactive compound(s) act to absorb UV radiation. The absorption process causes a photoactive compound to reach an excited state, wherein the excited state is characterized by the presence of excited electronic energy (e.g., singlet state energy or triplet state energy), as compared to the ground state of the photoactive compound. Once a photoactive compound reaches an excited state there exists a number of pathways by which the excited photoactive compound can dissipate its excess energy (e.g., singlet and/or triplet energy), however, many of those pathways destroy the photoactive compound and render it useless for its intended purpose. The alkoxycrylene compounds described herein accept electronic singlet excited state energy from retinoid compounds as well as Avobenzone, octyl methoxycinnamate (Octinoxate), octyl salicylate (Octisalate), and combinations thereof. The alkoxycrylenes also are very effective UVA absorbers in addition to providing electronic singlet state energy quenching of other UV-absorbing compounds in sunscreen compositions. As described in this assignee's pending application Ser. Nos. 11/891,281 and 12/022,758 filed on Aug. 9, 2007 and Jan. 30, 2008, respectively, the alkoxycrylene molecules described herein are especially effective photostabilizers when combined with one or more additional electronic singlet excited state quenching compounds such as oxybenzone. Particularly surprising photostabilization is achieved in sunscreen compositions containing the alkoxycrylene compounds described herein together with octyl methoxycinnamate and Avobenzone, all of which are useful, alone or in combination with the alkoxycrylene compounds of formula (I) and one or more retinoid compounds, as described herein.

A photoactive compound is one that responds to light photoelectrically. In the retinoid compound-containing compositions and methods of photostabilization disclosed herein, a photoactive compound is one that responds to UV radiation photoelectrically. For example, all photoactive compound-containing compositions that respond to UV radiation photoelectrically by photoactive compound photodegradation benefit highly by the inclusion of the alkoxycrylene molecules described herein. The alkoxycrylenes described herein are useful photostabilizers and/or photoactive compounds when combined with any single or combination photoactive compounds identified in Shaath, Nadim, Encyclopedia of UV filters, ©2007, hereby incorporated by reference. Photostability is a problem with all UV filters because they all reach an electronic singlet excited state upon exposure to UV radiation.

In addition to photostabilizing retinoid compounds, the compounds of formula (I) are theorized to also photostabilize the following UV filters contained in retinoid compound-containing compositions, including all of the following, including combinations of any two or more, and including compounds selected from the following categories (with specific examples) including: p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl(homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3 benzylidene, 4 methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxy-naphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid derivatives; vilouric acid derivatives; tannic acid and its derivatives; hydroquinone; and benzophenones (oxybenzone, sulisobenzone, dioxybenzone, benzoresorcinol, octabenzone, 4-isopropyldibenzoylmethane, butylmethoxydibenzoylmethane, etocrylene, and 4-isopropyl-dibenzoylmethane).

The following UV filters contained in retinoid compound-containing compositions should be particularly photostabilized by the alkoxycrylene molecules described herein: 2-ethylhexyl p-methoxycinnamate, 4,4'-t-butyl methoxydibenzoylmethane, octyldimethyl p-aminobenzoate, digalloyltrioleate, ethyl 4-[bis(hydroxypropyl)]aminobenzoate, 2-ethylhexylsalicylate, glycerol p-aminobenzoate, 3,3,5-trimethylcyclohexylsalicylate, and combinations thereof.

The photoactive retinoid compound-containing compositions disclosed herein can include a variety of additional photoactive compounds, preferably including one or more UV-A photoactive compounds and one or more UV-B photoactive compounds. Preferably, a retinoid compound-containing composition also includes a photoactive compound selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; uric acid derivatives; vilouric acid derivatives; tannic acid and derivatives thereof; hydroquinone; diethylamino hydroxybenzoyl hexyl benzoate and salts and derivatives thereof; and combinations of the foregoing.

UV A radiation (about 320 nm to about 400 nm), is recognized as contributing to causing damage to skin, particularly to very lightly colored or sensitive skin. A retinoid compound-containing sunscreen composition preferably includes a UV-A photoactive compound. Preferably, a retinoid compound-containing sunscreen composition includes a dibenzoylmethane derivative UV-A photoactive compound. Preferred dibenzoylmethane derivatives include, 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

For a product marketed in the United States, preferred dermatologically acceptable photoactive compounds and concentrations (reported as a percentage by weight of the total cosmetic sunscreen composition) include: aminobenzoic acid (also called para aminobenzoic acid and PABA; 15% or less), Avobenzone (also called butyl methoxy dibenzoylmethane; 3% or less), cinoxate (also called 2 ethoxyethyl p methoxycinnamate; 3% or less), dioxybenzone (also called benzophenone 8; 3% or less), homosalate ((also called 3,3,5-trimethylcyclohexyl salicylate, 15% or less), menthyl anthranilate (also called menthyl 2 aminobenzoate; 5% or less), octocrylene (also called 2 ethylhexyl 2 cyano 3,3 diphenylacrylate; 10% or less), octyl methoxycinnamate (7.5% or less), octyl salicylate (also called 2 ethylhexyl salicylate; 5% or less), oxybenzone (also called benzophenone 3; 6% or less), padimate O (also called octyl dimethyl PABA; 8% or less), phenylbenzimidazole sulfonic acid (water soluble; 4% or less), sulisobenzone (also called benzophenone 4; 10% or less), titanium dioxide (25% or less), trolamine salicylate (also called triethanolamine salicylate; 12% or less), and zinc oxide (25% or less).

Other preferred dermatologically acceptable photoactive compounds and preferred concentrations (percent by weight of the total cosmetic sunscreen composition) include diethanolamine methoxycinnamate (10% or less), ethyl-[bis(hydroxypropyl)]aminobenzoate (5% or less), glyceryl aminobenzoate (3% or less), 4 isopropyl dibenzoylmethane (5% or less), 4 methylbenzylidene camphor (6% or less), terephthalylidene dicamphor sulfonic acid (10% or less), and sulisobenzone (also called benzophenone 4, 10% or less).

For a product marketed in the European Union, preferred dermatologically acceptable photoactive compounds and preferred concentrations (reported as a percentage by weight of the total cosmetic sunscreen composition) include: PABA (5% or less), camphor benzalkonium methosulfate (6% or less), homosalate (10% or less), benzophenone 3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), benzylidene camphor sulfonic acid (6% or less, expressed as acid), octocrylene (10% or less, expressed as acid), polyacrylamidomethyl benzylidene camphor (6% or less), ethylhexyl methoxycinnamate (10% or less), PEG 25 PABA (10% or less), isoamyl p methoxycinnamate (10% or less), ethylhexyl triazone (5% or less), drometrizole trielloxane (15% or less), diethylhexyl butamido triazone (10% or less), 4 methylbenzylidene camphor (4% or less), 3 benzylidene camphor (2% or less), ethylhexyl salicylate (5% or less), ethylhexyl dimethyl PABA (8% or less), benzophenone 4 (5%, expressed as acid), methylene bis benztriazolyl tetramethylbutylphenol (10% or less), disodium phenyl dibenzimidazole tetrasulfonate (10% or less, expressed as acid), bis ethylhexyloxyphenol methoxyphenol triazine (10% or less), methylene bisbenzotriazolyl tetramethylbutylphenol (10% or less, also called TINOSORB M or Bisoctrizole), and bisethylhexyloxyphenol methoxyphenyl triazine. (10% or less, also called TINOSORB S or Bemotrizinol).

All of the above described UV filters are commercially available. For example, suitable commercially available organic UV filters are identified by trade name and supplier in the table below.

| CTFA Name | Trade Name | Supplier |
|---|---|---|
| benzophenone-3 | UVINUL M-40 | BASF Chemical Co. |
| benzophenone-4 | UVINUL MS-40 | BASF Chemical Co. |
| benzophenone-8 | SPECTRA-SORB UV-24 | American Cyanamid |
| DEA-methoxycinnamate | BERNEL HYDRO | Bernel Chemical |
| diethylamino hydroxybenzoyl hexyl benzoate | UVINUL A-PLUS | BASF Chemical Co. |
| diethylhexyl butamido triazone | UVISORB HEB | 3V-Sigma |
| disodium phenyl dibenzylimidazole | NEO HELIOPAN AP | Symrise |
| ethyl dihydroxypropyl-PABA | AMERSCREEN P | Amerchol Corp. |
| glyceryl PABA | NIPA G.M.P.A. | Nipa Labs. |
| homosalate | KEMESTER HMS | Humko Chemical |
| menthyl anthranilate | SUNAROME UVA | Felton Worldwide |
| octocrylene | UVINUL N-539 | BASF Chemical Co. |
| octyl dimethyl PABA | AMERSCOL | Amerchol Corp. |
| octyl methoxycinnamate | PARSOL MCX | Bernel Chemical |
| PABA | PABA | National Starch |
| 2-phenylbenzimidazole-5-sulphonic acid | EUSOLEX 6300 | EM Industries |
| TEA salicylate | SUNAROME W | Felton Worldwide |
| 2-(4-methylbenzildene)-camphor | EUSOLEX 6300 | EM Industries |
| benzophenone-1 | UVINUL 400 | BASF Chemical Co. |
| benzophenone-2 | UVINUL D-50 | BASF Chemical Co. |
| benzophenone-6 | UVINUL D-49 | BASF Chemical Co. |
| benzophenone-12 | UVINUL 408 | BASF Chemical Co. |
| 4-isopropyl dibenzoyl methane | EUSOLEX 8020 | EM Industries |
| butyl methoxy dibenzoyl methane | PARSOL 1789 | Givaudan Corp. |
| etocrylene | UVINUL N-35 | BASF Chemical Co. |
| methylene bisbenzotriazolyl tetramethylbutylphenol | TINOSORB M | Ciba Specialty Chemicals |
| bisethylhexyloxyphenol methoxyphenyl triazine | TINOSORB S | Ciba Specialty Chemicals |

Commonly-assigned U.S. Pat. Nos. 6,485,713 and 6,537,529, the disclosures of which are hereby incorporated herein by reference, describe compositions and methods for increasing the photostability of photoactive compounds in a sunscreen composition, e.g., by the addition of polar solvents to the oil phase of a composition. By increasing the polarity of the oil phase of a retinoid compound-containing sunscreen composition including the alkoxycrylenes described herein, e.g., methoxycrylene, the stability of the retinoid compound-containing sunscreen composition is surprisingly increased in comparison to octocrylene. In retinoid compound-containing sunscreen compositions, preferably, one or more of a highly polar solvent is present in the oil-phase of the composition. Preferably, a sufficient amount of a polar solvent is present in the retinoid compound-containing sunscreen composition to raise the dielectric constant of the oil-phase of the composition to a dielectric constant of at least about 7, preferably at least about 8. With or without the highly polar solvent in the oil phase, the alkoxycrylene molecules (e.g. methoxycrylene) described herein yield unexpected photostability in comparison to octocrylene.

Commonly assigned pending application Ser. Nos. 11/891,281 and 12/022,758 filed on Aug. 9, 2007 and Jan. 30, 2008, respectively describe a method of photostabilizing a photon-excited photoactive compound that reaches a singlet excited state when exposed to UV radiation in a sunscreen composition. The method comprises the steps of (1) mixing the photoactive compound with a compound of formula (I):

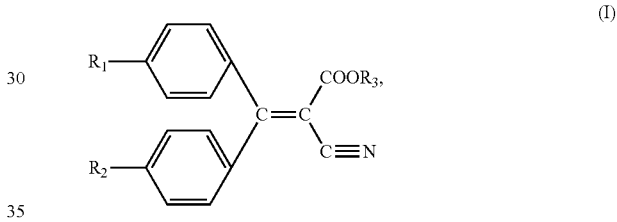

wherein one of $R_1$ and $R_2$ is a straight or branched chain $C_1$-$C_{12}$ alkoxy radical, and the non-alkoxy $R_1$ or $R_2$ is hydrogen and $R_3$ is a straight or branched chain $C_1$-$C_{24}$ alkyl radical, and (2) exposing the mixture to UV radiation in an amount sufficient for the photoactive compound to reach an electronic singlet excited state. The compound of formula (I) accepts the singlet excited state energy from the excited photoactive compound, allowing the photoactive compound to return to its ground state so that it is capable of absorbing additional UV radiation before undergoing a photochemical reaction destructive to its UV-absorbing capability. Thus, the singlet excited state energy from the photon-excited photoactive compound is quenched through transfer from the photon-excited photoactive compound to the compound of formula (I), thereby photostabilizing the photoactive compound.

A photoactive compound can be considered stable when, for example, after 30 MED irradiation the photoactive compound has retained at least about 90% of its original absorbance at a wavelength, or over a range of wavelengths of interest (e.g., the wavelength at which a photoactive compound has a peak absorbance, such as 290-400 nm for isotretinoin). Likewise, a retinoid compound-containing composition can include a plurality of photoactive compounds. A retinoid compound-containing composition, as a whole, can be considered stable when, for example, after 30 MED irradiation the retinoid compound-containing composition has retained at least about 90% of its original absorbance at one or more wavelengths of interest (e.g., at or near the peak absorbance wavelength of the primary photoactive compound).

It has surprisingly been found that the alkoxycrylene compounds of formula (I) described herein unexpectedly and significantly increase the photostability of a retinoid compound in a composition by at least 3-fold and as much as 10-fold or greater. The ability of the alkoxycrylene compounds to stabilize retinoid compounds is concentration dependent, with the amount of retinoid compound photostabilization increasing with the concentration of the alkoxycrylene compound. For example, the percentages of retinol remaining in compositions comprising 0.1% retinol and either 1% or 4% ethylhexyl methoxycrylene were 70% and 99%, respectively, after irradiation with 6×5 MED.

It has also surprisingly been found that the alkoxycrylene compounds of formula (I) described herein are unexpectedly more effective at stabilizing a retinoid compound than the commonly used photostabilizer, octocrylene (OC). For example, the percentage of retinol remaining in a composition comprising 0.10% retinol and 4% ethylhexyl methoxycrylene was 99% after irradiation with 6×5 MED, while the percentage of retinol remaining in a composition comprising 0.10% retinol and 4% octocrylene was only 78%.

In accordance with one important embodiment, an alkoxycrylene compound of formula (I) is combined in an anti-acne, anti-aging, wrinkle reducing, sunscreen or dermatological composition with a retinoid compound. The group of retinoid compounds advantageous according to the invention is defined as including all dermatologically and/or pharmaceutically acceptable retinoid compounds, including retinol and its esters, retinal and also retinoic acid (vitamin A acid) and esters thereof. Examples of retinoid compounds include retinol, retinal, isotretinoin, tretinoin, alitretinoin, etretinate, acitretin, bexarotene, tazarotene, adapalene). In specific embodiments, the retinoid compound is selected from the group consisting of isotretinoin and retinol.

The total amount of the retinoid compound in the finished retinoid compound-containing composition is chosen from about 0.001% by weight to about 5% by weight, preferably from about 0.005% by weight to about 1% by weight, for example from about 0.01% by weight to about 0.5% by weight, in each case based on the total weight of the composition.

The alkoxycrylene compound is a compound of formula (I):

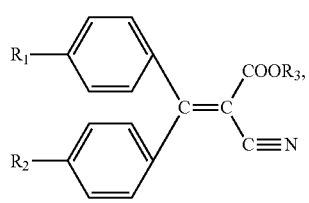

wherein one of $R_1$ and $R_2$ is a straight or branched chain $C_1$-$C_{12}$ alkoxy radical, and the non-alkoxy $R_1$ or $R_2$ is hydrogen and $R_3$ is a straight or branched chain $C_1$-$C_{24}$ alkyl radical. In a specific embodiment, the compound of formula (I) is ethylhexyl methoxycrylene (EHMC, IV).

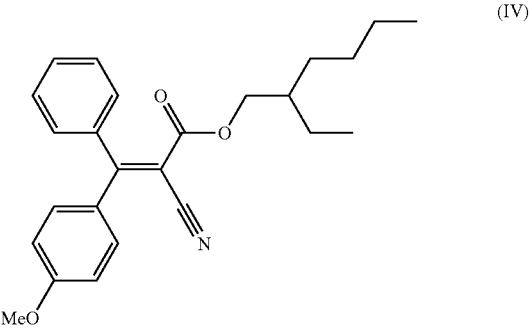

In another specific embodiment, the compound of formula (I) is butyloctyl methoxycrylene (BOMeOC, V).

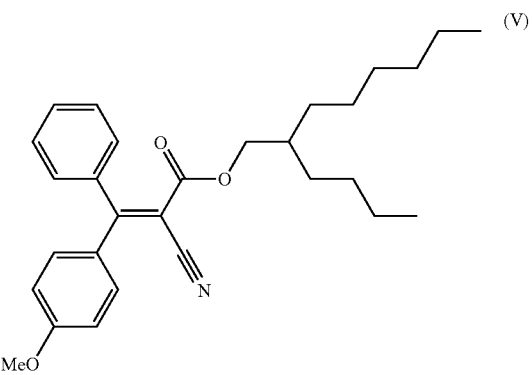

The total amount of the alkoxycrylene compound in the finished retinoid compound-containing composition is chosen from the range of about 0.01% by weight to about 20% by weight, preferably from about 0.1 to about 10% by weight, for example from about 0.1% to about 5% by weight, in each case based on the total weight of the composition.

The molar ratio of the alkoxycrylene compound to the retinoid compound in the finished retinoid compound-containing composition is from about 0.001 to about 1, preferably from about 0.005 to about 0.1, for example, from about 0.01 to about 0.06.

In accordance with another embodiment, an alkoxycrylene compound of formula (I) is combined in a retinoid compound-containing anti-acne, anti-aging, wrinkle reducing, sunscreen or dermatological composition with a water soluble UV filter compound and/or a broad-band filter compound and optionally, but preferably, together with a dibenzoylmethane derivative and/or a dialkyl naphthalate.

Advantageous water-soluble UV filter substances for the purposes of the present invention are sulfonated UV filters, in particular:
phenylene-1,4-bis(2-benzimidazyl)-3,3'-5,5'-tetrasulfonic acid, which has the following structure:

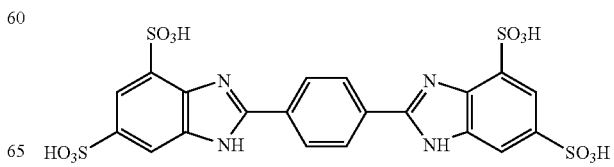

and its salts, especially the corresponding sodium, potassium or triethanolammonium salts, in particular phenylene-1,4-bis (2-benzimidazyl)-1-3,3'-5,5'-tetrasulfonic acid bissodium salt

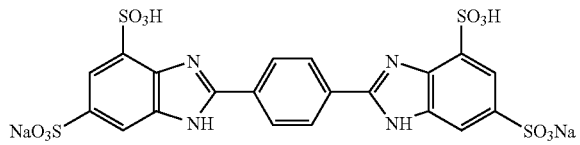

with the INCI name disodium phenyl dibenzimidazole tetrasulfonate (CAS No.: 180898-37-7), which is obtainable for example under the proprietary name Neo Heliopan A P from Haarmann & Reimer.

Further advantageous sulfonated UV filters for the purposes of the present invention are the salts of 2-phenylbenzimidazole-5-sulfonic acid, such as its sodium, potassium or its triethanolammonium salts, and the sulfonic acid itself

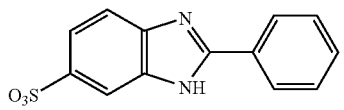

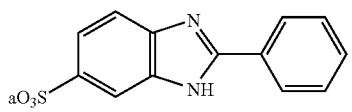

with the INCI name phenylbenzimidazole sulfonic acid (CAS No. 27503-81-7), which is obtainable for example under the proprietary name Eusolex 232 from Merck or under Neo Heliopan Hydro from Haarmann & Reimer.

Further advantageous water-soluble UV-B and/or broadband filter substances for the purposes of the present invention are, for example, sulfonic acid derivatives of 3-benzylidenecamphor, such as, for example, 4-(2-oxo-3-bornylidenemethyl)benzene-sulfonic acid, 2-methyl-5-(2-oxo-3-bornylidenemethyl)sulfonic acid and the salts thereof.

The total amount of one or more water-soluble UV filter substances in the finished retinoid compound-containing anti-acne, anti-aging, wrinkle reducing, cosmetic or dermatological composition is advantageously chosen from the range of about 0.01% by weight to about 20% by weight, preferably from about 0.1 to about 10% by weight.

In accordance with another embodiment, an alkoxycrylene compound of formula (I) is combined in a retinoid compound-containing anti-acne, anti-aging, wrinkle reducing, sunscreen or dermatological composition with a hydroxybenzophenone compound and/or a broad-band filter compound and optionally, but preferably, together with a dibenzoylmethane derivative and/or a dialkyl naphthalate.

With an alkoxycrylene, it is possible to completely dispense with the use of other UV stabilizers, in particular the use of ethylhexyl-2-cyano-3,3-diphenylacrylate(octocrylene) or 4-methylbenzylidenecamphor.

Hydroxybenzophenones are characterized by the following structural formula:

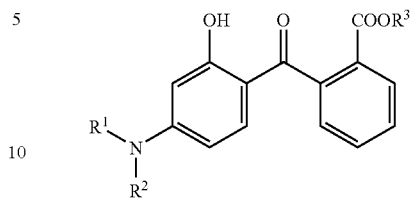

where $R^1$ and $R^2$ independent of one another are hydrogen, $C_1$-$C_{20}$-alkyl, $C_3$-$C_{10}$-cycloalkyl or $C_3$-$C_{10}$-cyloalkenyl, wherein the substituents $R^1$ and $R^2$ together with the nitrogen atom to which they are bound can form a 5- or 6-ring and $R^3$ is a $C_1$-$C_{20}$ alkyl radical.

A particularly advantageous hydroxybenzophenone is the 2-(4'-diethylamino-2'-hydroxybenzoyl)benzoic acid hexyl ester (also: aminobenzophenone) which is characterized by the following structure:

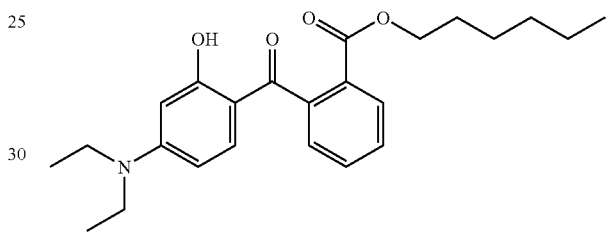

and is available from BASF under the Uvinul A Plus.

According to the invention, retinoid compound-containing anti-acne, anti-aging, wrinkle-reducing, cosmetic or dermatological compositions contain about 0.1 to about 20% by weight, advantageously from about 0.1 to about 15% by weight, very particularly preferred from about 0.1 to about 10% by weight, of one or more hydroxybenzophenones, in each case based on the total weight of the compositions.

Within the scope of the present invention, dialkyl naphthalates for which $R^1$ and/or $R^2$ represent branched alkyl groups with 6 to 10 carbon atoms are advantageously included in the retinoid-compound containing compositions. Within the scope of the present invention diethylhexyl naphthalate is very particularly preferred which is available, e.g., under the trade name Hallbrite TQ™ from CP Hall or Corapan TQ™ from H&R.

According to another embodiment of the invention, retinoid compound-containing anti-acne, anti-aging, wrinkle reducing, cosmetic or dermatological compositions advantageously contain about 0.001 to about 30% by weight, preferably from about 0.01 to about 20% by weight, very particularly preferred from about 0.5 to about 15% by weight, of one or more dialkyl naphthalates.

The retinoid compound-containing anti-acne, anti-aging, wrinkle reducing, cosmetic or dermatological UV radiation-protection compositions according to the invention can be composed as usual and be used for anti-acne, anti-aging, wrinkle reducing, cosmetic or dermatological light-protection, furthermore for the treatment, care and cleansing of the skin and/or hair and as a cosmetic product in decorative cosmetics.

In accordance with another important embodiment, an alkoxycrylene compound of formula (I) is combined in a retinoid compound-containing anti-acne, anti-aging, wrinkle reducing, sunscreen or dermatological composition with a benzotriazole derivatives compound and/or a broad-band filter compound and optionally, but preferably, together with a dibenzoylmethane derivative and/or a dialkyl naphthalate.

An advantageous benzotriazole derivative is 2,2'-methylenebis(6-(2H-benzotriazol-2-yl)-4-(1,1,3,3-tetramethylbutyl)phenol), which has the chemical structural formula

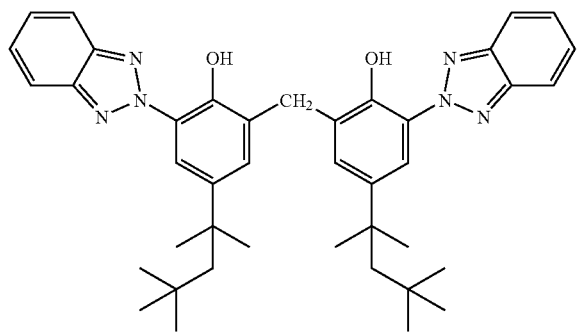

(INC1: bisoctyltriazole). It is obtainable under the proprietary name Tinosorb® from CIBA-Chemikalien GmbH and is distinguished by good UV absorption properties. The disadvantage of this substance is the characteristic of forming imperceptibly thin films on the skin which have unpleasant tactile properties.

Another disadvantage is that such benzotriazole derivatives show only inadequate solubility, if any, in conventional oil components. Well-known solvents can dissolve only up to a maximum of about 15% by weight of these compounds, which usually corresponds to a concentration of about 1 to 1.5% by weight of dissolved (=active) filter substance in the complete cosmetic or dermatological composition.

One disadvantage of the prior art is accordingly that generally only comparatively low sun protection factors have been achievable with these filter substances because their solubility or dispersibility in the compositions is too low, i.e. they can be satisfactorily incorporated into such compositions only with difficulty or not at all.

Even if it is also possible in principle to achieve a certain UV protection when the solubility is limited, another problem frequently occurs, that is recrystallization.

Substances of low solubility in particular recrystallize comparatively rapidly, which may be induced by fluctuations in temperature or other influences. Uncontrolled recrystallization of an essential ingredient of a composition such as a UV filter has, however, extremely disadvantageous effects on the properties of the given composition and, not least, on the desired light protection.

In accordance with another embodiment, the retinoid compound-containing compositions described herein can contain an increased content of unsymmetrically substituted triazine derivatives when combined together with an alkoxycrylene compound of formula (I) to obtain an increased sun protection factor.

It was, however, surprising and not predictable for the skilled worker that the disadvantages of the prior art are remedied by active ingredient combinations effective for UV light protection in a retinoid compound-containing composition and composed of
(a) one or more UV filter substances selected from the group of benzotriazole derivatives;
(b) an alkoxycrylene of formula (I); and optionally (c) one or more dialkyl naphthalates having the structural formula:

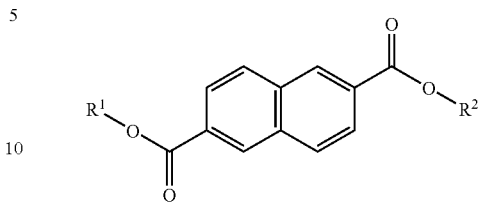

in which $R^1$ and $R^2$ are, independently of one another, selected from the group of branched and unbranched alkyl groups having 6 to 24 carbon atoms.

Particularly advantageous UV light protection filters for the purpose of this embodiment of the present invention include a benzotriazole compound having a structural formula:

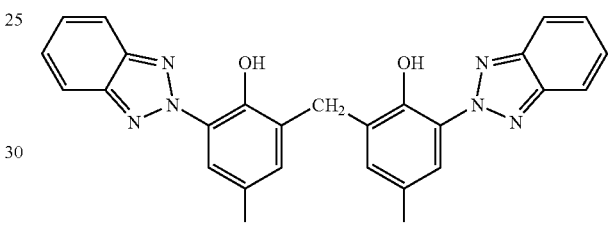

where $R_1$ and $R_2$ are, independently of one another, selected from the group of branched or unbranched $C_1$-$C_{18}$-alkyl radicals, of $C_5$-$C_{12}$-cycloalkyl or aryl radicals which are optionally substituted by one or more $C_1$-$C_4$ alkyl groups.

The preferred benzotriazole derivative is 2,2'-methylenebis(6-(2H-benzotriazol-2-yl)-4-(1,1,3,3-tetramethylbutyl)phenol) which is characterized by the chemical structural formula:

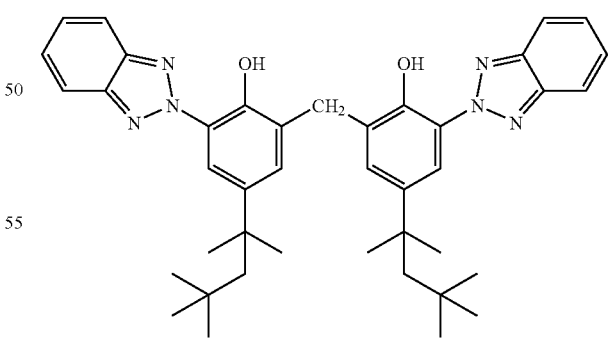

An advantageous broadband filter for the purpose of the present invention is moreover 2-(2H-benzotriazol-2-yl)-4-methyl-6-[2-methyl-3-[1,3,3,3-tetramethyl-1-[(trimethylsilyl)oxy]disiloxanyl]propyl]phenol (CAS No.: 155633-54-8) with the INC1 name drometrizole trisiloxane, which is characterized by the chemical structural formula

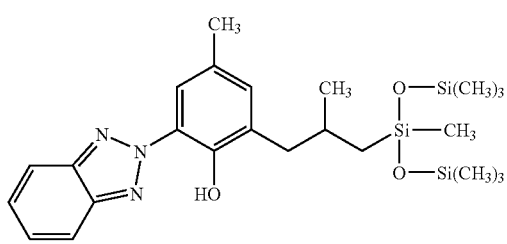

The total amount of one or more benzotriazole derivatives, in particular of 2,2'-methylenebis(6-(2H-benzotriazol-2-yl)-4-(1,1,3,3-tetramethylbutyl)phenol) and/or 2-(2H-benzotriazol-2-yl)-4-methyl-6-[2-methyl-3-[1,3,3,3-tetramethyl-1-[(trimethylsilyl)oxy]disiloxa-nyl]propyl]phenol, in the finished retinoid compound-containing anti-acne, anti-aging, wrinkle reducing, cosmetic or dermatological compositions is advantageously chosen from the range from 0.1 to 15.0% by weight, preferably 0.5 to 10.0% by weight, based on the total weight of the compositions.

The retinoid compound-containing compositions according to the invention can be composed as usual and can be used for anti-acne, anti-aging, wrinkle reducing, cosmetic or dermatological UV light-protection purposes, furthermore for the treatment, care and cleansing of the skin and/or hair and as a cosmetic product in decorative cosmetics.

For use, the retinoid compound-containing compositions can be applied to the skin and/or the hair in a sufficient quantity in the manner customary for retinoid compound-containing compositions.

The retinoid compound-containing compositions according to the invention can comprise cosmetic auxiliaries such as those conventionally used in such compositions, e.g. preservatives, bactericides, perfumes, antifoams, dyes, pigments which have a coloring effect, thickeners, moisturizers and/or humectants, fats, oils, waxes or other conventional constituents of an anti-acne, anti-aging, wrinkle reducing, cosmetic or dermatological composition, such as alcohols, polyols, polymers, foam stabilizers, electrolytes, organic solvents or silicone derivatives.

An additional content of antioxidants is generally preferred. According to the invention, favorable antioxidants which can be used together with one or more retinoid compounds are any antioxidants suitable or conventional for anti-acne, anti-aging, wrinkle reducing, cosmetic and/or dermatological applications.

The antioxidants are particularly advantageously chosen from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. .alpha.-carotene, .beta.-carotene, lycopene) and derivatives thereof, chlorogenic acid and derivatives thereof, lipoic acid and derivatives thereof (e.g. dihydrolipoic acid), aurothioglucose, propylethiouracil and other thiols (e.g. thioredoxin, glutathione, cysteine, cystine, cystamine and the glycosyl, N-acetyl, methyl, ethyl, propyl, amyl, butyl and lauryl, palmitoyl, oleoyl, .gamma.-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very low tolerated doses (e.g. pmol to .mu.mol/kg), and also (metal) chelating agents (e.g. alpha.-hydroxy fatty acids, palmitic acid, phytic acid, lactoferrin), .alpha.-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. gamma.-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of gum benzoin, rutinic acid and derivatives thereof, .alpha.-glycosylrutin, ferulic acid, furfurylideneglucitol, carnosine, butylhydroxytoluene, butylhydroxyanisole, nordihydroguairetic acid, trihydroxybutyro-phenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

In accordance with another embodiment, the retinoid compound-containing compositions containing an alkoxycrylene compound of formula (I) according to the invention are combined with hydrophilic skincare active ingredients and/or a broad-band filter compound and optionally, but preferably, together with a dibenzoylmethane derivative.

Advantageous hydrophilic active ingredients which (individually or in any combinations with one another) are stabilized by their use together with an alkoxycrylene in a retinoid compound-containing composition according to the invention include those listed below:

biotin; carnitine and derivatives; creatine and derivatives; folic acid; pyridoxine; niacinamide; polyphenols (in particular flavonoids, very particularly alpha-glucosylrutin); ascorbic acid and derivatives; Hamamelis; Aloe Vera; panthenol; amino acids.

Particularly advantageous hydrophilic active ingredients for the purposes of this embodiment of the present invention are also water-soluble antioxidants, such as, for example, vitamins.

The amount of hydrophilic active ingredients (one or more compounds) in the retinoid compound-containing compositions is preferably about 0.0001 to about 10% by weight, particularly preferably about 0.001 to about 5% by weight, based on the total weight of the composition.

Particularly advantageous retinoid compound-containing compositions are also obtained when antioxidants are used as additives or active ingredients. According to this embodiment of the invention, the retinoid compound-containing compositions advantageously comprise one or more antioxidants. Favorable, but nevertheless optional antioxidants which may be used are all antioxidants customary or suitable for anti-acne, anti-aging, wrinkle reducing, cosmetic and/or dermatological applications.

The amount of antioxidants (one or more compounds) in the compositions is preferably about 0.001 to about 30% by weight, particularly preferably about 0.05 to about 20% by weight, in particular about 0.1 to about 10% by weight, based on the total weight of the composition.

If vitamin E and/or derivatives thereof are the antioxidant or antioxidants, it is advantageous to choose their respective concentrations from the range from about 0.001 to about 10% by weight, based on the total weight of the composition.

It is particularly advantageous when the retinoid compound-containing compositions according to the present invention comprise further anti-acne, anti-aging, wrinkle reducing, cosmetic or dermatological active ingredients, preferred active ingredients being antioxidants which can protect the skin against oxidative stress.

Advantageous further active ingredients are natural active ingredients and/or derivatives thereof, such as e.g. ubiquinones, carotenoids, creatine, taurine and/or .beta.-alanine.

Retinoid compound-containing compositions according to the invention, which comprise e.g. known antiwrinkle active ingredients, such as flavone glycosides (in particular .alpha.-glycosylrutin), coenzyme Q10, vitamin E and/or derivatives and the like, are particularly advantageously suitable for the prophylaxis and treatment of cosmetic or dermatological changes in skin, as arise, for example, during skin aging (such as, for example, dryness, roughness and formation of dryness wrinkles, itching, reduced refatting (e.g. after washing), visible vascular dilations (teleangiectases, couperosis), flaccidity and formation of wrinkles and lines, local hyperpigmentation, hypopigmentation and abnormal pigmentation (e.g. age spots), increased susceptibility to mechanical stress (e.g. cracking) and the like). In addition, they are advantageously suitable against the appearance of dry or rough skin.

In accordance with still another important embodiment, an alkoxycrylene compound of formula (I) is combined in a retinoid compound-containing anti-acne, anti-aging, wrinkle reducing, sunscreen or dermatological composition with particulate UV filter substances and/or a broad-band filter compound and optionally, but preferably, together with a dibenzoylmethane derivative and/or a dialkyl naphthalate.

Preferred particulate UV filter substances for the purposes of this embodiment of the present invention are inorganic pigments, especially metal oxides and/or other metal compounds which are slightly soluble or insoluble in water, especially oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides, and the sulfate of barium ($BaSO_4$).

Zinc oxides for the purposes of the present invention may also be used in the form of commercially available oily or aqueous predispersions. Zinc oxide particles and predispersions of zinc oxide particles which are suitable according to the invention are distinguished by a primary particle size of <300 nm and can be obtained under the following proprietary names from the stated companies:

Particularly preferred zinc oxides for the purposes of the invention are Z-Cote HP1 and Z-Cote from BASF and zinc oxide NDM from Haarmann & Reimer.

Titanium dioxide pigments useful in this embodiment of the invention may be in the form of both the rutile and anatase crystal modification and may for the purposes of the present invention advantageously be surface-treated ("coated"), the intention being for example to form or retain a hydrophilic, amphiphilic or hydrophobic character. This surface treatment may consist of providing the pigments by processes known per se with a thin hydrophilic and/or hydrophobic inorganic and/or organic layer. The various surface coatings may for the purposes of the present invention also contain water.

Inorganic surface coatings for the purposes of the particulate sunscreen additive embodiment of the present invention may consist of aluminum oxide ($Al_2O_3$), aluminum hydroxide $Al(OH)_3$ or aluminum oxide hydrate (also: alumina, CAS No.: 1333-84-2), sodium hexametaphosphate $(NaPO_3)_6$, sodium metaphosphate $(NaPO_3)_n$, silicon dioxide ($SiO_2$) (also: silica, CAS No.: 7631-86-9), or iron oxide ($Fe_2O_3$). These inorganic surface coatings may occur alone, in combination and/or in combination with organic coating materials.

Organic surface coatings for the purposes of the particulate sunscreen additive embodiment of the present invention may consist of vegetable or animal aluminum stearate, vegetable or animal stearic acid, lauric acid, dimethylpolysiloxane (also: dimethicones), methylpolysiloxane (methicones), simethicones (a mixture of dimethylpolysiloxane with an average chain length of from 200 to 350 dimethylsiloxane units and silica gel) or alginic acid. These organic surface coatings may occur alone, in combination and/or in combination with inorganic coating materials.

Coated and uncoated titanium dioxides of the particulate sunscreen additive embodiment of the invention may be used in the form of commercially available oily or aqueous predispersions. It may be advantageous to add dispersion aids and/or solubilization mediators.

Suitable titanium dioxide particles and predispersions of titanium dioxide particles for the purposes of the particulate sunscreen additive embodiment of the present invention are obtainable under the following proprietary names from the stated companies:

| Proprietary name | Coating | Manufacturer |
|---|---|---|
| Z-Cote HP1 | 2% Dimethicone | BASF |
| Z-Cote | / | BASF |
| ZnO NDM | 5% Dimethicone | H&R |
| ZnO Neutral | / | H&R |
| MZ-300 | / | Tayca Corporation |
| MZ-500 | / | Tayca Corporation |
| MZ-700 | / | Tayca Corporation |
| MZ-303S | 3% Methicone | Tayca Corporation |
| MZ-505S | 5% Methicone | Tayca Corporation |
| MZ-707S | 7% Methicone | Tayca Corporation |
| MZ-303M | 3% Dimethicone | Tayca Corporation |
| MZ-505M | 5% Dimethicone | Tayca Corporation |
| MZ-707M | 7% Dimethicone | Tayca Corporation |
| Z-Sperse Ultra | ZnO (>=56%)/Ethylhexyl Hydroxystearate Benzoate/ Dimethicone/Cyclomethicone | Collaborative Laboratories |
| Samt-UFZO-450/D5 (60%) | ZnO (60%)/Cyclomethicone/ Dimethicone | Miyoshi Kasei |

| Proprietary name | Coating | Additional ingredients of the predispersion | Manufacturer |
|---|---|---|---|
| MT-150W | None | — | Tayca Corporation |
| MT-150A | None | — | Tayca Corporation |
| MT-500B | None | — | Tayca Corporation |
| MT-600B | None | — | Tayca Corporation |
| MT-100TV | Aluminum hydroxide Stearic acid | — | Tayca Corporation |
| MT-100Z | Aluminum hydroxide Stearic acid | — | Tayca Corporation |
| MT-100T | Aluminum hydroxide Stearic acid | — | Tayca Corporation |
| MT-500T | Aluminum hydroxide Stearic acid | — | Tayca Corporation |

-continued

| Proprietary name | Coating | Additional ingredients of the predispersion | Manufacturer |
|---|---|---|---|
| MT-100S | Aluminum hydroxide Lauric acid | — | Tayca Corporation |
| MT-100F | Stearic acid Iron oxide | — | Tayca Corporation |
| MT-100SA | Alumina Silica | — | Tayca Corporation |
| MT-500SA | Alumina Silica | — | Tayca Corporation |
| MT-600SA | Alumina Silica | — | Tayca Corporation |
| MT-100SAS | Alumina Silica Silicone | — | Tayca Corporation |
| MT-500SAS | Alumina Silica Silicone | — | Tayca Corporation |
| MT-500H | Alumina | — | Tayca Corporation |
| MT-100AQ | Silica Aluminum hydroxide Alginic acid | — | Tayca Corporation |
| Eusolex T | Water Simethicone | — | Merck KgaA |
| Eusolex T-2000 | Alumina Simethicone | — | Merck KgaA |
| Eusolex T-Olio F | Silica Dimethylsilate Water | $C_{12-15}$ Alkylbenzoate Calcium Polyhydroxystearate Silica Dimethylsilate | Merck KgaA |
| Eusolex T-Olio P | Water Simethicone | Octyl Palmitate PEG-7 Hydrogenated Castor Oil Sorbitan Oleate Hydrogenated Castor Oil Beeswax Stearic acid | Merck KgaA |
| Eusolex T-Aqua | Water Alumina Sodium metaphosphate | Phenoxyethanol Sodium Methylparabens Sodium metaphosphate | Merck KgaA |
| Eusolex T-45D | Alumina Simethicone | Isononyl Isononanuate Polyglyceryl Ricinoleate | Merck KgaA |
| Kronos 1171 (Titanium dioxide 171) | None | — | Kronos |
| Titanium dioxide P25 | None | — | Degussa |
| Titanium dioxide T805 | Octyltrimethylsilane (Uvinul TiO$_2$) | — | Degussa |
| UV-Titan X610 | Alumina Dimethicone | — | Kemira |
| UV-Titan X170 | Alumina Dimethicone | — | Kemira |
| UV-Titan X161 | Alumina Silica Stearic acid | — | Kemira |
| UV-Titan M210 | Alumina | — | Kemira |
| UV-Titan M212 | Alumina | Glycerol | Kemira |
| UV-Titan M262 | Alumina Silicone | — | Kemira |
| UV-Titan M160 | Alumina Silica Stearic acid | — | Kemira |
| Tioveil AQ 10PG | Alumina Silica | Water Propylene glycol | Solaveil Uniquema |
| Mirasun TiW 60 | Alumina Silica | Water | Rhone-Poulenc |

The titanium dioxides of the particulate sunscreen additive embodiment of the invention are distinguished by a primary particle size between 10 nm to 150 nm.

Titanium dioxides particularly preferred for the purposes of the particulate sunscreen additive embodiment of the present invention are MT-100 Z and MT-100 TV from Tayca Corporation, Eusolex T-2000 from Merck and titanium dioxide T 805 from Degussa.

Further advantageous pigments are latex particles. Latex particles which are advantageous according to the particulate sunscreen additive embodiment of the invention are described in the following publications: U.S. Pat. No. 5,663,213 and EP 0 761 201. Particularly advantageous latex particles are those formed from water and styrene/acrylate copolymers and available for example under the proprietary name "Alliance SunSphere" from Rohm & Haas.

An advantageous organic pigment for the purposes of the particulate sunscreen additive embodiment of the present invention is 2,2'-methylenebis(6-(2H-benzotriazol-2-yl)-4-(1,1,3,3-tetramethylbutyl-)phenol) (INCI: bis-octyltriazol), which is obtainable under the proprietary name Tinosorb® M from CIBA-Chemikalien GmbH.

It is particularly advantageous for the purposes of the particulate sunscreen additive embodiment of the present invention for particulate UV filter substances which are not already in the form of a predispersion first to be dispersed in one or more dialkyl naphthalates of the invention and for this basic dispersion then to be further processed. Whereas auxiliaries which may enter into unwanted interactions with other substances of the retinoid compound-containing anti-acne, anti-aging, wrinkle reducing, cosmetic or dermatological composition are usually added for stabilization to commercially available predispersions, it is astonishingly possible to dispense with the addition of such stabilizers when preparing basic dispersions of the invention.

In accordance with another embodiment, one or more water-soluble UV filter substances can be combined with the retinoid-compound containing composition. The total amount of one or more water-soluble UV filter substances in the finished retinoid compound-containing anti-acne, anti-aging, wrinkle reducing, cosmetic or dermatological composition is advantageously chosen from the range of about 0.01% by weight to about 20% by weight, preferably from about 0.1 to about 10% by weight, in each case based on the total weight of the preparations.

In accordance with still another important embodiment, an alkoxycrylene compound of formula (I) is combined in a retinoid compound-containing anti-acne, anti-aging, wrinkle reducing, sunscreen or dermatological composition with asymmetrically substituted triazine UV filter compounds and/or a broad-band filter compound and optionally, but preferably, together with a dibenzoylmethane derivative.

Asymmetrically substituted triazine derivatives display a good UV light protection effect. Their main disadvantage is, however, that their solubility is low in conventional oil components. Well-known solvents can dissolve only up to a maximum of about 15% by weight of these compounds, which usually corresponds to a concentration of about 1 to about 1.5% by weight of dissolved (=active) filter substance in the complete retinoid compound-containing anti-acne, anti-aging, wrinkle reducing, cosmetic or dermatological composition.

One disadvantage of the prior art is accordingly that generally only comparatively low sun protection factors have been achievable with these filter substances because their solubility or dispersibility in the compositions is too low, i.e. they can be satisfactorily incorporated into such compositions only with difficulty or not at all.

Even if it is also possible in principle to achieve a certain UV protection when the solubility is limited, another problem frequently occurs, that is recrystallization. Substances of low solubility in particular recrystallize comparatively rapidly, which may be induced by fluctuations in temperature or other influences. Uncontrolled recrystallization of an essential ingredient of a composition such as a UV filter has, however, extremely disadvantageous effects on the properties of the given composition and, not least, on the desired light protection.

Disadvantages of the prior art are remedied by active ingredient combinations effective for UV light protection in a retinoid compound-containing composition and composed of:

(a) one or more UV filter substances selected from the group of asymmetrically substituted triazine derivatives, and (b) one or more alkoxycrylenes having the structural formula (I); and (c) optionally a dibenzoylmethane derivative and/or a dialkyl naphthalate.

Advantageous asymmetrically substituted s-triazine derivatives within the meaning of this embodiment of the present invention are, for example, those described in EP-A-570 838, whose chemical structure is represented by the generic formula

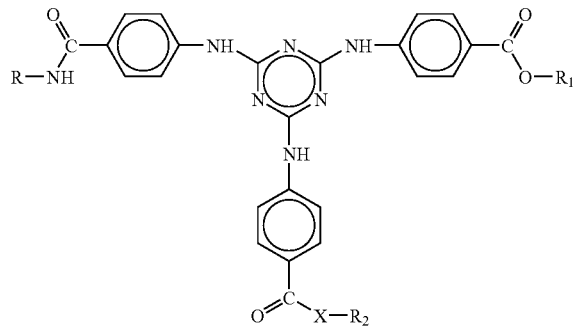

where

R is a branched or unbranched $C_1$-$C_{18}$-alkyl radical, a $C_5$-$C_{12}$-cycloalkyl radical, optionally substituted by one or more $C_1$-$C_4$-alkyl groups, and X is an oxygen atom or an NH group, $R_1$ is a branched or unbranched $C_1$-$C_8$-alkyl radical, a $C_5$-$C_{12}$-cycloalkyl radical, optionally substituted by one or more $C_1$-$C_4$-alkyl groups, or a hydrogen atom, an alkali metal atom, an ammonium group or a group of the formula

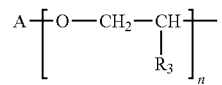

in which

A is a branched or unbranched $C_1$-$C_{18}$-alkyl radical, a $C_5$-$C_{12}$-cycloalkyl or aryl radical, optionally substituted by one or more $C_1$-$C_4$-alkyl groups, $R_3$ is a hydrogen atom or a methyl group, n is a number from 1 to 10, $R_2$ is a branched or unbranched $C_1$-$C_{18}$-alkyl radical, a $C_5$-$C_{12}$-cycloalkyl radical, optionally substituted by one or more $C_1$-$C_4$-alkyl groups, and if X is the NH group, a branched or unbranched $C_1$-$C_{18}$-alkyl radical, a $C_5$-$C_{12}$-cycloalkyl radical, optionally substituted by one or more $C_1$-$C_4$-alkyl groups, or a hydrogen atom, an alkali metal atom, an ammonium group or a group of the formula

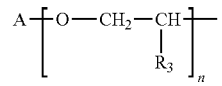

in which

A is a branched or unbranched $C_1$-$C_{18}$-alkyl radical, a $C_5$-$C_{12}$-cycloalkyl or aryl radical, optionally substituted by one or more $C_1$-$C_4$-alkyl groups, $R_3$ is a hydrogen atom or a methyl group, n is a number from 1 to 10, if X is an oxygen atom.

In a preferred form of this triazine embodiment, the retinoid compound-containing compositions are anti-acne, anti-aging, wrinkle reducing, sunscreen, cosmetic or dermatological compositions that include a content of least one asymmetrically substituted s-triazine selected from the group of substances having the following structural formula:

and/or

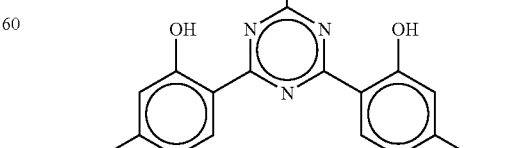

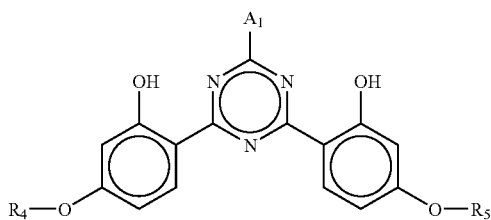

All the bisresorcinyltriazines, are advantageous for this embodiment of the purpose of the present invention. $R_4$ and $R_5$ are very particularly advantageously selected from the group of branched or unbranched alkyl groups of 1 to 18 carbon atoms. The alkyl groups may also again advantageously be substituted by silyloxy groups.

$A_1$ is advantageously a substituted homocyclic or heterocyclic aromatic five-membered ring or six-membered ring.

The following compounds are very particularly advantageous:

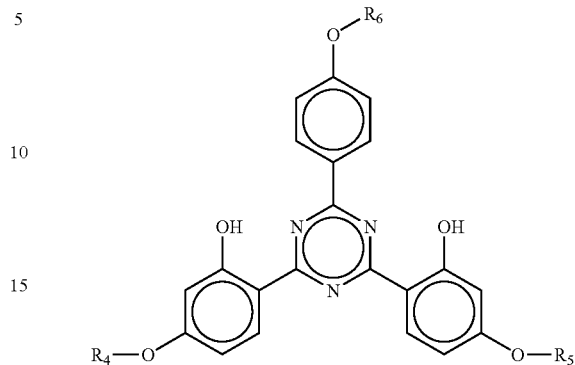

where $R_6$ is a hydrogen atom or a branched or unbranched alkyl group with 1 to 10 carbon atoms, in particular 2,4-bis{[4-(2-ethylhexyloxy)-2-hydroxy]phenyl}-6-(4-methoxyphenyl)-1,3,5-triazine (INCI: aniso triazine), which is obtainable under the proprietary name Tinosorb® S from CIBA-Chemikalien GmbH and is characterized by the following structure:

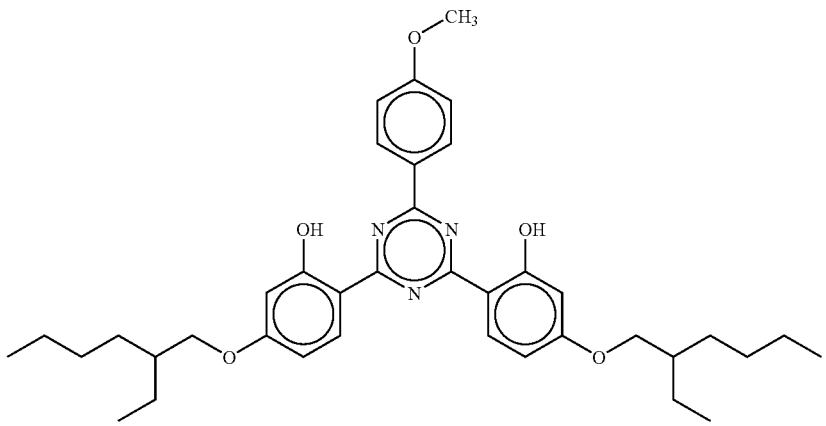

Also advantageous is 2,4-bis{[4-(3-sulfonato-2-hydroxypropyloxy)-2-hydroxy]phenyl}-6-(4-methoxyphenyl)-1,3,5-triazine sodium salt, which is characterized by the following structure:

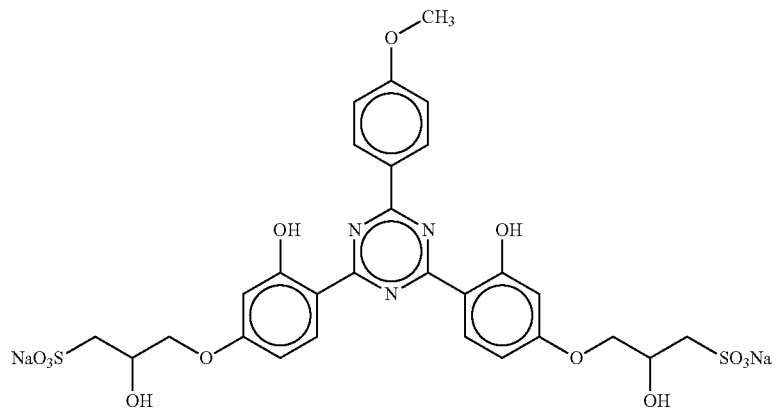

Also advantageous is 2,4-bis{[4-(3-(2-propyloxy)-2-hydroxypropyloxy)-2-hydroxy]phenyl}-6(4-methoxyphenyl)-1,3,5-triazine, which is characterized by the following structure:

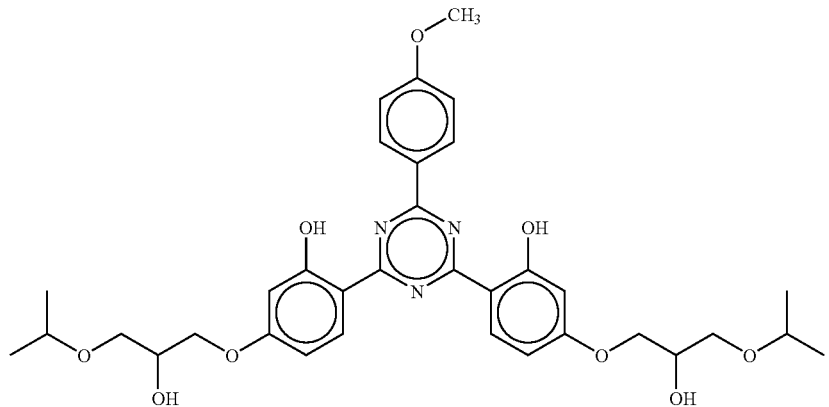

Also advantageous is 2,4-bis{[4-(2-ethylhexyloxy)-2-hydroxy]phenyl}-6-[4-(2-methoxyethoxycarbonyl)phenylamino]-1,3,5-triazine, which is characterized by the following structure:

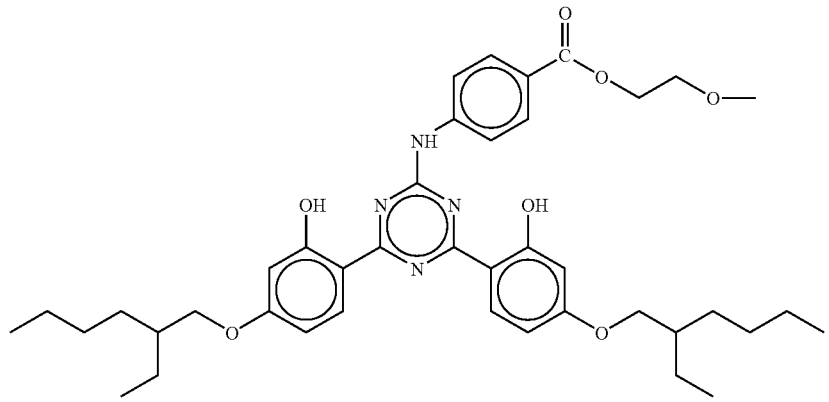

Also advantageous is 2,4-bis{[4-(3-(2-propyloxy)-2-hydroxypropyloxy)-2-hydroxy]phenyl}-6-[4-(ethoxycarbonyl)phenylamino]-1,3,5-triazine which is characterized by the following structure:

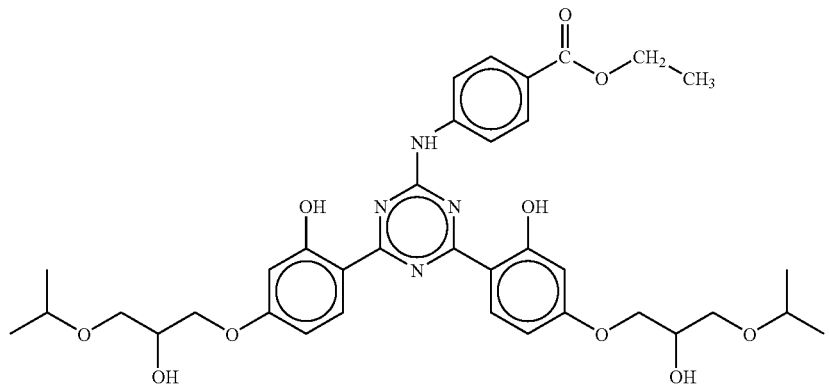

Also advantageous is 2,4-bis{[4-(2-ethylhexyloxy)-2-hydroxy]phenyl}-6-(1-methylpyrrol-2-yl)1,3,5-triazine, which is characterized by the following structure:

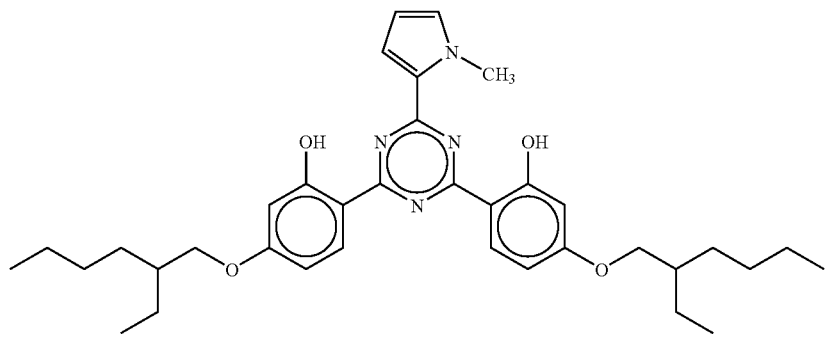

Also advantageous is 2,4-bis{[4-tris(trimethylsiloxysilyl-propyloxy)-2-hydroxy]phenyl}-6-(4-methoxyphenyl)-1,3,5-triazine, which is characterized by the following structure:

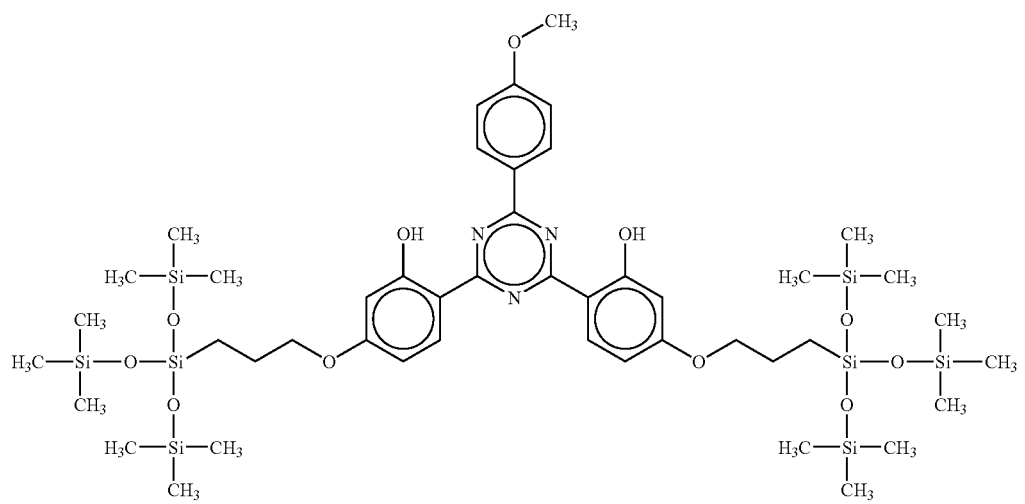

Also advantageous is 2,4-bis{[4-(2-methylpropenyloxy)-2-hydroxy]phenyl}-6-(4-methoxyphenyl)-1,3,5-triazine, which is characterized by the following structure:

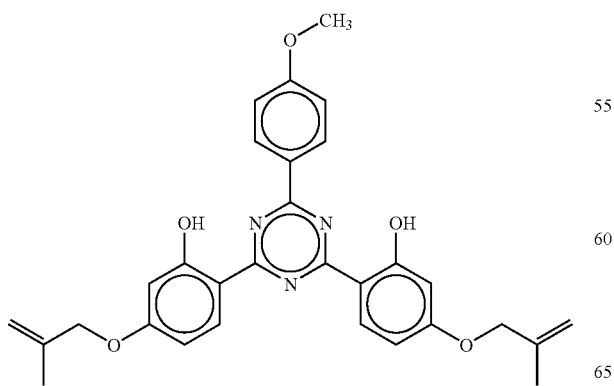

Also advantageous is 2,4-bis{[4-(1',1',1',3',5',5',5'-heptamethylsiloxy-2-methylpropyloxy)-2-hydroxy]-phenyl}-6-(4-methoxyphenyl)-1,3,5-triazine, which is characterized by the following structure:

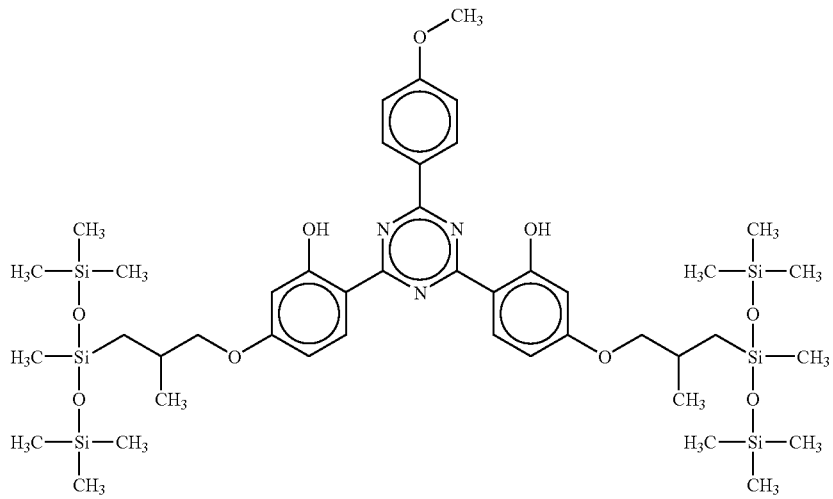

In a particularly preferred embodiment, the present invention relates to retinoid compound-containing anti-acne, anti-aging, wrinkle reducing, cosmetic or dermatological compositions with a content of an asymmetrically substituted s-triazine whose chemical structure is represented by the formula

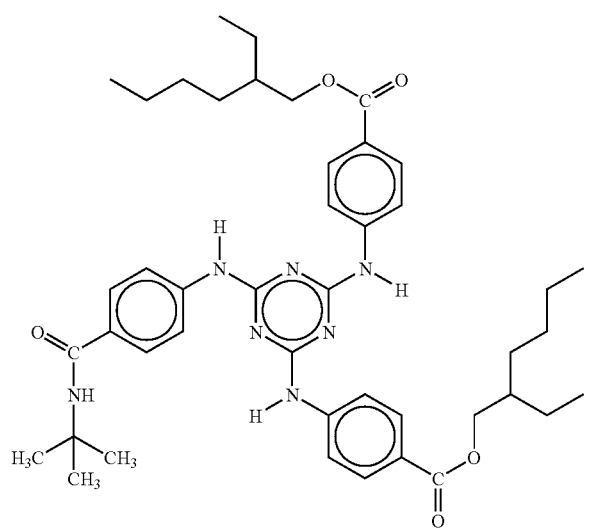

which is also referred to hereinafter as dioctylbutylamidotriazone (INCI) and is obtainable under the proprietary name UVASORB HEB from Sigma 3 V.

The asymmetrically substituted s-triazine derivative(s) are advantageously incorporated into the oil phase of the retinoid compound-containing anti-acne, anti-aging, wrinkle reducing, cosmetic or dermatological compositions.

The total amount of one or more asymmetrically substituted s-triazine derivatives, in particular of dioctylbutylamidotriazone, in the finished retinoid compound-containing anti-acne, anti-aging, wrinkle reducing, cosmetic or dermatological composition is advantageously chosen from the range from about 0.1 to about 15.0% by weight, preferably about 0.5 to about 10.0% by weight, based on the total weight of the compositions.

The retinoid compound-containing anti-acne, anti-aging, wrinkle reducing, cosmetic or dermatological light protection compositions described herein may include conventional additives, solvents, and water concentrations when used for anti-acne, anti-aging, wrinkle reducing, cosmetic or dermatological light protection and for the treatment, care and cleansing of skin and/or the hair and as a make-up product in decorative cosmetics.

In accordance with another important embodiment, an alkoxycrylene compound of formula (I) is combined in a retinoid compound-containing anti-acne, anti-aging, wrinkle reducing, sunscreen or dermatological composition with a lipophilic oxidation or UV-sensitive active ingredients and/or a broad-band filter compound and optionally, but preferably, together with a dibenzoylmethane derivative.

Advantageous lipophilic active ingredients which are stabilized in an excellent manner when used with the alkoxycrylenes described herein by the use according to the invention are those whose log P value is greater than 3.5. P is the partition coefficient, which is defined as the ratio of the equilibrium concentration of a dissolved substance in a two-phase system which consists of two solvents which are essentially immiscible with one another. These two solvents are, in the present case, n-octanol and water, i.e.

$$P_{ow} = \frac{C_{n-octanol}}{C_{water}}$$

It is advantageous to choose the lipophilic active ingredients from the group of ubiquinones and plastoquinones. For the purposes of the present invention, coenzyme Q10, which has a log P value of about 15, is very particularly advantageous.

It was particularly surprising that very advantageous compositions according to this embodiment of the present invention can be obtained when the lipophilic ingredient(s) is/are chosen only from the group of ubiquinones.

Further lipophilic acid ingredients advantageous according to this embodiment of the invention are carotenoids. For the purposes of the present invention, .beta.-carotene, which has a log P value of 15, for example, is particularly advantageous.

Further lipophilic active ingredients advantageous according to this embodiment of the invention are: lipoic acid and derivatives, vitamin E and derivatives, vitamin F, dioic acid [8-hexadecene-1,16-dicarboxylic acid (CAS number 20701-68-2)]

The amount of lipophilic active ingredients (one or more compounds) in the compositions is preferably about 0.0001 to about 10% by weight, particularly preferably about 0.001 to about 5% by weight, based on the total weight of the composition.

EXAMPLES

Example 1

Photostabilization of Isotretinoin with Butyloctyl Methoxycrylene

Oil-in-water emulsions comprising stabilized and unstabilized isotretinoin (Table 3) were prepared in dim light (and/or protected from light) according to the following procedure and irradiated with ultraviolet light to show the surprisingly superior photostabilizing effect of butyloctyl methoxycrylene (BOMeOC) on isotretinoin (IsoRA).

A second vessel was charged with ingredients #1-6, and 9, and heated to 70° C. Ingredient #7 was then added to the second vessel and the mixture was stirred until homogeneous. Approximately one-third of the solution from the first vessel was added to a main vessel. Ingredient #8 was then added to the main vessel with stirring, and the resulting mixture was heated to 65° C. The solution in the second vessel was then added to the main vessel and homogenized until an emulsion was fully formed. The main vessel was removed from heat, subjected to sweep stirring, and the rest of the solution in the first vessel was added to it. Ingredients #12 and 13 were premixed and then added to the main vessel, followed by ingredient #15. Sweep stirring was continued until the mixture was smooth and homogeneous. Q.S. water was added to the main vessel to replace the water lost during processing. The resulting composition was packaged after the batch cooled below 35° C.

Approximately 0.12 g of an isotretinoin composition from Table 3 was applied to a 5 cm×2.5 cm quartz slide and covered with a second 5 cm×2.5 cm quartz slide. Pressure was applied to the resulting slide sandwich to spread the isotretinoin composition evenly between the slides. The slide sandwich was then irradiated with 5 MED doses at six different locations (6×5 MED), each dose covering a one centimeter circle. The isotretinoin composition was then extracted from the slide

TABLE 3

Oil-in Water Emulsions Tested To Demonstrate the Photostabilization of Isotretionoin with Butyloctyl Methoxycrylene

| | # | Ingredients | Composition 1 0% BOMeOC | Composition 2 7% BOMeOC |
|---|---|---|---|---|
| Oil Phase | 1a | Butyloctyl methoxycrylene | 0.00% | 7.00% |
| | 1b | Isopropyl myristate | 7.00% | 0.00% |
| | 2 | Caprylic/capric triglycerides | 5.00% | 5.00% |
| | 3 | Phenyethyl benzoate | 5.00% | 5.00% |
| | 4 | Tocopherol | 0.14% | 0.14% |
| | 5 | BHT | 0.04% | 0.04% |
| | 6 | Isotretinoin, 98% | 0.05% | 0.05% |
| Emulsifiers | 7 | Ceralution H ®: Behenyl alcohol, Glyceryl stearate, Glyceryl stearate citrate, Sodium dicocoylethylenediamine PEG-15 sulfate | 1.00% | 1.00% |
| | 8 | Ceralution F ®: Sodium lauroyl lactylate, Sodium dicocoylethylenediamine PEG-15 sulfate | 1.00% | 1.00% |
| | 9 | Trideceth-12 | 1.00% | 1.00% |
| Water Phase | 10 | Xanthan gum | 0.15% | 0.15% |
| | 11 | Disodium EDTA | 0.10% | 0.10% |
| | 12 | Glycerin | 4.00% | 4.00% |
| | 13 | Mikrokill ® COS: Phenoxyethanol, Caprylyl glycol, Chlorphenesin | 1.00% | 1.00% |
| | 14 | Water | 72.17% | 72.17% |
| Other | 15 | Acrylamide, Sodium acryloyldimethyl taurate copolymer | 2.50% | 2.50% |
| | | Isotretinoin Remaining after 6 × 5 MED | 31% | 100% |

Disodium EDTA (11) was dissolved in a first vessel containing water (14). Xanthan gum (10) was added and the mixture was stirred to effect dissolution of the xanthan gum.

sandwich with a small amount of acetonitrile, mixed well, and filtered through a PTFE sample filter. HPLC was performed on a 50 μL sample of the extracted isotretinoin composition using the instrumentation and parameters in Table 4. The percentage of isotretinoin remaining in the composition after irradiation with 6×5 MED is shown in Table 3.

TABLE 4

HPLC Instrumentation and Parameters

| | |
|---|---|
| Instrumentation | Delta HPLC |
| Software | Agilent Technologies ChemStation for LC 3D |
| Column | Alltech Apollo C18, 150 * 1.6 mm (5u) |
| Mobile Phase | Acetonitrile/Water (80:20) |
| Flow Rate | 1.0 mL/min |
| Temperature | 30° C. |

Example 2

Photostabilization of Retinol with Ethylhexyl Methoxycrylene

Oil-in-water emulsions comprising retinol with different concentrations of photostabilizer (Table 5) were prepared in dim light (and/or protected from light) according to the following procedure and irradiated with ultraviolet light to show the surprisingly superior photostabilizing effect of ethylhexyl methoxycrylene (EHMC) on retinol.

TABLE 5

Oil-in Water Emulsions Tested To Demonstrate the Photostabilization of Retinol with Ethylhexyl Methoxycrylene

| | | | Composition | | | | |
|---|---|---|---|---|---|---|---|
| | | | 3<br>0%<br>EHMC | 4<br>1%<br>EHMC | 5<br>2%<br>EHMC | 6<br>4%<br>EHMC | 7<br>4%<br>OC |
| | # | Ingredients | | | | | |
| Oil Phase | 1a | Ethylhexyl methoxycrylene | 0.00% | 1.00% | 2.00% | 4.00% | 0.00% |
| | 1b | Octocrylene | 0.00% | 0.00% | 0.00% | 0.00% | 4.00% |
| | 1c | Isopropyl myristate | 4.00% | 3.00% | 2.00% | 0.00% | 0.00% |
| | 2 | Caprylic/capric triglycerides | 5.00% | 5.00% | 5.00% | 5.00% | 5.00% |
| | 3 | Phenyethyl benzoate | 5.00% | 5.00% | 5.00% | 5.00% | 5.00% |
| | 4 | Tocopherol | 0.14% | 0.14% | 0.14% | 0.14% | 0.14% |
| | 5 | BHT | 0.04% | 0.04% | 0.04% | 0.04% | 0.04% |
| | 6 | Trideceth-12 | 1.00% | 1.00% | 1.00% | 1.00% | 1.00% |
| | 7 | Retinol 99% | 0.10% | 0.10% | 0.10% | 0.10% | 0.10% |
| | 8 | Ceralution ® H: Behenyl alcohol, Glyceryl stearate, Glyceryl stearate citrate, Disodium ethylene dicocamide PEG-15 disulfate | 1.00% | 1.00% | 1.00% | 1.00% | 1.00% |
| Water Phase | 9 | Xanthan gum | 0.15% | 0.15% | 0.15% | 0.15% | 0.15% |
| | 10 | Ceralution F ®: Sodium lauroyl lactylate, Disodium ethylene dicocamide PEG-15 disulfate | 1.00% | 1.00% | 1.00% | 1.00% | 1.00% |
| | 11 | Mikrokill ® COS: Phenoxyethanol, Caprylyl glycol, Chlorphenesin | 1.00% | 1.00% | 1.00% | 1.00% | 1.00% |
| | 12 | Glycerin | 4.00% | 4.00% | 4.00% | 4.00% | 4.00% |
| | 13 | Disodium EDTA | 0.05% | 0.05% | 0.05% | 0.05% | 0.05% |
| Other | 14 | Simulgel 600 ™: Acrylamide, Sodium acryloyldimethyl taurate copolymer, Isohexadecane Polysorbate 80 (polyoxyethylene 20 sorbitan monooleate) | 2.50% | 2.50% | 2.50% | 2.50% | 2.50% |
| | 15 | Water | 75.02% | 75.02% | 75.02% | 75.02% | 75.02% |
| | | Retinol Remaining after 6 × 5 MED | 9% | 70% | 80% | 99% | 78% |

TABLE 4-continued

HPLC Instrumentation and Parameters

| | |
|---|---|
| Detector | UV Spectrophotometer at 230 nm |
| Pump Program | Isocratic, 40 min |
| Analysis Method | Internal standard and ratio |
| Internal standard | Dibutyl phthalate |

Disodium EDTA (13) was dissolved in a first vessel containing water (15). Xanthan gum (9) was added and the mixture was stirred to effect dissolution of the xanthan gum. A second vessel was charged with oils #1-3 and antioxidants #4-5. Retinol (8) was dissolved in the resulting oil phase while heating the solution to 65° C., and Ceralution H® (9) was then added with stirring. Approximately one-third of the solution from the first vessel was added to a main vessel. Ceralution F® (10) was then added to the main vessel with stirring and the resulting mixture was heated to 65° C. The solution in the second vessel was added to the main vessel and homogenized for two minutes. The balance of the solution in the first vessel was slowly added to the main vessel during homogenization. The main vessel was removed from heat and cooled using propeller stirring. Microkill® COS (11) and glycerin (12) were premixed and added to the main vessel. The stirring method was switched to sweep stirring and Simulgel 600™ (14) was added to the main vessel. The mixture was stirred until smooth and homogeneous.

Approximately 0.12 g of a retinol composition from Table 5 was applied to a 5 cm×2.5 cm quartz slide and covered with a second 5 cm×2.5 cm quartz slide. Pressure was applied to the resulting slide sandwich to spread the retinol composition evenly between the slides. The slide sandwich was then irradiated with 5 MED doses at six different locations (6×5 MED), each dose covering a one centimeter circle. The retinol composition was then extracted from the slide sandwich with a small amount of acetonitrile, mixed well, and filtered through a PTFE sample filter. HPLC was performed on a 50 μL sample of the extracted retinol composition using the instrumentation and parameters in Table 6.

TABLE 6

HPLC Instrumentation and Parameters

| | |
|---|---|
| Instrumentation | Delta HPLC |
| Software | Agilent Technologies ChemStation for LC 3D |
| Column | Alltech Apollo C18, 150 * 4.6 mm (5u) |
| Mobile Phase | Acetonitrile/Water (80:20) |
| Injection | 10 μL |
| Flow Rate | 1.0 mL/min |
| Temperature | 30° C. |
| Detector | UV Spectrophotometer at 230, 350, and 330 nm |
| Pump Program | Isocratic, 15 min |

Retinol standards were prepared by accurately weighing 0.02, 0.03, 0.04, and 0.05 g of retinol separately into four different 25-mL volumetric flasks. Approximately 10 to 15 mL of acetonitrile was added to each flask, the flasks were shaken until the retinol was well dissolved and then diluted to volume with acetonitrile. The solution was mixed well and filtered through PTFE sample filters. The retinol standards were subjected to HPLC according to the parameters in Table 6 and a chart was constructed of the peak height and/or peak area versus the weight (grams per 25 mL) of the standards. The retention time for retinol was 13.7 min.

A retinol control sample was prepared by accurately weighing 3.0 to 3.2 g of the unirradiated retinol composition into a 25-mL volumetric flask. Approximately 10 to 15 mL of acetonitrile was added to the flask, the flask was shaken until the retinol sample was completely dissolved, and then diluted to volume with acetonitrile. The solution was mixed well and filtered through a PTFE sample filter. The retinol control sample was subjected to HPLC according to the parameters in Table 6 and the number grams per 25 mL (N) was determined for the sample by comparing the peak height and/or peak area of the sample to the retinol standard chart. The percentage of retinol present in the unirradiated sample was calculated according to equation 1.

$$\% \text{ Retinol} = N/W * 100 \quad (1)$$

N=number of grams per 25 mL determined from the retinol standard chart
W=sample weight (grams per 25 mL)

The percentage of retinol remaining in the retinol composition after irradiation with 6×5 MED was calculated based on the ratios of retinol and an internal peak at a chosen UV wavelength before and after radiation. The results are shown in Table 5.

The invention claimed is:

1. A method of protecting a retinoid compound in a sunscreen or dermatological composition that reaches a singlet excited state or fluoresces when exposed to UV radiation from UV-induced photodegradation comprising combining the retinoid compound with a compound of formula (I) in an amount of at least 0.1%, based on the total weight of the composition, to quench singlet excited state energy from the retinoid compound and transfer the singlet excited state energy from the retinoid compound to the compound of formula (I),

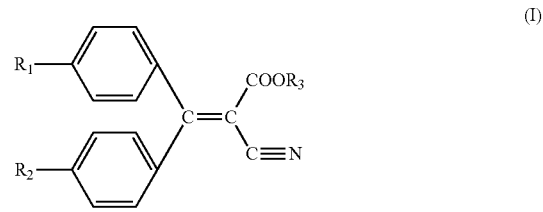

wherein one of $R_1$ and $R_2$ is a straight or branched chain $C_1$-$C_{30}$ alkoxy radical, and the non-alkoxy $R_1$ or $R_2$ is hydrogen; and $R_3$ is a straight or branched chain $C_1$-$C_{30}$ alkyl radical, thereby photostabilizing the retinoid compound.

2. The method of claim 1, wherein $R_1$ is methoxy and $R_2$ is hydrogen.

3. The method of claim 1, wherein $R_1$ is hydrogen and $R_2$ is methoxy.

4. The method of claim 1, wherein $R_3$ is a $C_{12}$-$C_{24}$ straight chain or branched alkyl.

5. The method of claim 4, wherein $R_3$ is a 2-butyloctyl radical.

6. The method of claim 4, wherein $R_3$ is an 2-ethylhexyl radical.

7. The method of claim 1, wherein the compound of formula (I) is present in an amount in the weight range of about 0.1% to about 20%, based on the total weight of the composition.

8. The method of claim 7, wherein the compound of formula (I) is present in an amount in this weight range of about 0.1% to about 10%, based on the total weight of the composition.

9. The method of claim 7, wherein the compound of formula (I) is present in an amount in this weight range of about 0.1% to about 5%, based on the total weight of the composition.

10. The method of claim 1, wherein the retinoid compound is present in an amount in the weight range of about 0.001% to about 5%, based on the total weight of the composition.

11. The method of claim 10, wherein the retinoid compound is present in this weight range of about 0.005% to about 1%, based on the total weight of the composition.

12. The method of claim 10, wherein the retinoid compound is present in this weight range of about 0.01% to about 0.5%, based on the total weight of the composition.

13. The method of claim 1, wherein a molar ratio of the retinoid compound to the compound of formula (I) is about 0.001 to about 1.

14. The method of claim 13, wherein the molar ratio of the retinoid compound to the compound of formula (I) is about 0.005 to about 0.1.

15. The method of claim 13, wherein the molar ratio of the retinoid compound to the compound of formula (I) is about 0.01 to about 0.06.

16. The method of claim 1, wherein the retinoid compound is selected from the group consisting of retinol, retinal, tretinoin, isotretinoin, alitretinoin, etretinate, and acitretin.

17. The method of claim 16, wherein the retinoid compound is retinol.

18. The method of claim 16, wherein the retinoid compound is isotretinoin.

19. The method of claim 16, wherein the retinoid compound is tretinoin.

20. The method of claim 16, wherein the retinoid compound is retinal.

21. The method of claim 16, wherein the retinoid compound is alitretinoin.

22. The method of claim 16, wherein the retinoid compound is etretinate.

23. The method of claim 16, wherein the retinoid compound is acitretin.

24. The method of claim 1, wherein said composition further comprises a lipophilic active compound in an amount of about 0.001 wt % to about 10 wt %, based on the total weight of the composition.

25. The method of claim 24, wherein the lipophilic active compound is in an amount of about 0.001 wt % to about 5 wt %, based on the total weight of the composition.

26. The method of claim 24, wherein the lipophilic active compound is selected from the group consisting of ubiquinones and plastoquinones.

27. The method of claim 24, wherein the lipophilic active compound is coenzyme Q10.

28. The method of claim 1, wherein the retinoid compound is an ester of retinoic acid.

29. The method of claim 1, wherein the retinoid compound is bexarotene.

30. The method of claim 1, wherein the retinoid compound is tazarotene.

31. The method of claim 1, wherein the retinoid compound is adapalene.

* * * * *